(12) United States Patent
Zhong et al.

(10) Patent No.: US 10,301,279 B2
(45) Date of Patent: May 28, 2019

(54) PIPERIDINE CARBOXAMIDE COMPOUND, PREPARATION METHOD, AND USE THEREOF

(71) Applicant: Institute of Pharmacology and Toxicology Academy of Military Medical Sciences P.L.A. China, Beijing (CN)

(72) Inventors: Wu Zhong, Beijing (CN); Song Li, Beijing (CN); Yanqun Zeng, Beijing (CN); Junhai Xiao, Beijing (CN); Xinbo Zhou, Beijing (CN); Zhibing Zheng, Beijing (CN); Xingzhou Li, Beijing (CN); Xiaokui Wang, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 0 days.

(21) Appl. No.: 15/794,666

(22) Filed: Oct. 26, 2017

(65) Prior Publication Data
US 2018/0044321 A1 Feb. 15, 2018

Related U.S. Application Data

(62) Division of application No. 15/104,875, filed as application No. PCT/CN2014/094314 on Dec. 19, 2014, now Pat. No. 9,840,489.

(30) Foreign Application Priority Data

Dec. 20, 2013 (CN) .......................... 2013 1 0704743

(51) Int. Cl.
| | |
|---|---|
| *A61K 31/506* | (2006.01) |
| *C07D 401/04* | (2006.01) |
| *C07D 401/14* | (2006.01) |
| *C07D 409/14* | (2006.01) |
| *A61K 45/06* | (2006.01) |
| *A61K 31/404* | (2006.01) |
| *A61K 31/454* | (2006.01) |
| *A61K 31/4545* | (2006.01) |
| *A61K 31/517* | (2006.01) |
| *A61K 31/5377* | (2006.01) |

(52) U.S. Cl.
CPC .......... *C07D 401/04* (2013.01); *A61K 31/404* (2013.01); *A61K 31/454* (2013.01); *A61K 31/4545* (2013.01); *A61K 31/506* (2013.01); *A61K 31/517* (2013.01); *A61K 31/5377* (2013.01); *A61K 45/06* (2013.01); *C07D 401/14* (2013.01); *C07D 409/14* (2013.01)

(58) Field of Classification Search
CPC .. C07D 401/04; C07D 409/14; C07D 401/14; A61K 31/4545; A61K 45/06; A61K 31/404; A61K 31/5377; A61K 31/517; A61K 31/454; A61K 31/506
See application file for complete search history.

(56) References Cited

U.S. PATENT DOCUMENTS

| | | | |
|---|---|---|---|
| 2010/0331294 A1 | 12/2010 | Black et al. | |
| 2016/0333002 A1 | 11/2016 | Zhong et al. | |

FOREIGN PATENT DOCUMENTS

| | | |
|---|---|---|
| CA | 2811796 A1 | 3/2012 |
| CN | 101578275 A | 11/2009 |
| CN | 102227220 A | 10/2011 |
| CN | 103097354 A | 5/2013 |
| CN | 105143210 A | 12/2015 |
| CN | 105829304 A | 8/2016 |
| EP | 3 085 701 A1 | 10/2016 |
| WO | WO 02/45652 A2 | 6/2002 |
| WO | WO 03/074500 A2 | 9/2003 |
| WO | WO 2005/026149 A1 | 3/2005 |
| WO | WO 2006/113704 A2 | 10/2006 |
| WO | WO 2007/031529 A1 | 3/2007 |
| WO | WO 2007/067629 A1 | 6/2007 |
| WO | WO 2008/008895 A1 | 1/2008 |
| WO | WO 2008/020622 A1 | 2/2008 |
| WO | WO 2008/054702 A1 | 5/2008 |

(Continued)

OTHER PUBLICATIONS

Tenover, Am J Infect Control, vol. 34, No. 5, Supplement I, pp. S3-S10 (Year: 2006).*

(Continued)

*Primary Examiner* — Sudhakar Katakam
(74) *Attorney, Agent, or Firm* — Sterne, Kessler, Goldstein & Fox P.L.L.C.

(57) ABSTRACT

The present invention provides a compound of a general formula I, a stereomeride, pharmaceutically acceptable salt or a solvate thereof, a preparation method thereof, and usages in preparing medicines for preventing and/or treating diseases or symptoms caused by drug-resistant tumors or drug-resistant bacteria and in preparing medicines for preventing and/or treating diseases or symptoms related to tumors, neurodegenerative diseases, allogeneic transplantation rejection, and infection. Preferably, the diseases or symptoms related to tumors, neurodegenerative diseases, allogeneic transplantation rejection, and infection are diseases or symptoms caused by a heat shock protein 70 (Hsp70). The compound in the present invention is used for overcoming a difficult problem of drug resistance of tumors, improves the effect of tumor treatment, and provides a new medical strategy for clinical tumor treatment.

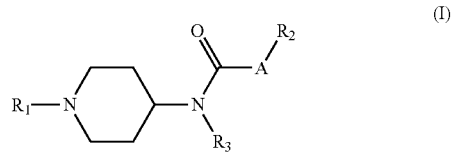

(I)

4 Claims, No Drawings

(56) References Cited

FOREIGN PATENT DOCUMENTS

| WO | WO 2010/060940 | A2 | 6/2010 |
|----|----------------|----|--------|
| WO | WO 2011/101304 | A2 | 8/2011 |
| WO | WO 2012/016082 | A1 | 2/2012 |
| WO | WO 2012/038081 | A1 | 3/2012 |
| WO | WO 2012/078777 | A1 | 6/2012 |
| WO | WO 2014/175621 | A1 | 10/2014 |
| WO | WO 2015/090226 | A1 | 6/2015 |
| WO | WO 2016/077375 | A1 | 5/2016 |

OTHER PUBLICATIONS

Roberti et al, J.Cell. Physiol., 207:571-581 (Year: 2006).*
Ramp et al, Histol Histopathol, 22:1099-1107 (Year: 2007).*
International Search Report (ISR) for PCT/CN2014/094314; I.A. fd: dated Dec. 19, 2014, dated Mar. 25, 2015, State Intellectual Property Office of the P.R. China, Beijing, China.
International Preliminary Report on Patentability (IPRP) including the Written Opinion of the International Searching Authority (PCT Rule 44bis) for PCT/CN2014/094314; I.A. fd: dated Dec. 19, 2014, dated Jun. 21, 2016, by the International Bureau of WIPO, Geneva, Switzerland.
Office action and Search Report for CN Appl. No. 2014800695691, dated May 17, 2017 by the State Intellectual Property Office of the P.R. China, Beijing, China.
STN Database: CAS Registry Nos. (RN) 1261232-35-2 (entered Feb. 1, 2011); 1261233-55-9 (entered Feb. 1, 2011); 1261234-79-0 (entered Feb. 1, 2011); 1261234-84-7 (entered Feb. 1, 2011); 1353989-76-0 (entered Jan. 24, 2012); and 1773538-38-7 (entered Jun. 4, 2015), STN International, Columbus, OH, accessed May 8, 2017.
Extended European search report including the supplementary European search report and the European search opinion, dated May 4, 2017, for EP Application No. 14871647, European Patent Office, Munich, Germany.
Excerpted file history of U.S. Appl. No. 15/104,875 (now U.S. Pat. No. 9,840,489), Zhong et al., through Nov. 21, 2017, US Patent and Trademark Office, Alexandria, VA.

\* cited by examiner

PIPERIDINE CARBOXAMIDE COMPOUND, PREPARATION METHOD, AND USE THEREOF

CROSS REFERENCE TO RELATED APPLICATION

This application claims the benefit of U.S. patent application Ser. No. 15/104,875, 371 date Jul. 20, 2016, which is hereby incorporated by reference in its entirety.

TECHNICAL FIELD

The present invention is in the field of medicine, and specifically relates to novel piperidine carboxamide compound, preparation method, and use thereof.

BACKGROUND ART

Heat shock protein 70 (Hsp70) is widely present in nucleus, cytoplasm, endoplasmic reticulum, mitochondria and chloroplast cells, and is involved in intracellular protein de novo synthesis, orientation, protein maturation and degradation of misfolded proteins, thus affecting the growth and metabolism function of cells. In cells, Hsp70 binding tonascent polypeptides on ribosome can prevent misfolding of nascent polypeptides; Hsp70 is essential for remodeling clathrin in the process of pinocytosis of mammalian cells; and Hsp70 binding to non native conformation proteins can promote proper folding and assembly of proteins, and can maintain extended conformation of protein precursors and prevent their aggregation denaturation and degradation, allowing easy transport to organelles.

Studies have shown that, Hsp70 is related to many diseases, such as tumors, neurodegenerative diseases, allograft rejection or infection and the like. In cancer cells, Hsp70 affects apoptosis mainly through the following pathways: (1) mitochondrial pathway: in the early stage of mitochondria, Hsp70 blocks migration of Bax, and decreases permeability of mitochondrial outer membrane, thereby inhibiting the release of cytc and AIF from mitochondria; in the late stage of mitochondria, Hsp70 binds directly to Apaf1, blocks the aggregation of procaspase-9, so that apoptotic body cannot be formed, and caspase-3 downstream cannot be activated; (2) death receptor pathway: Hsp70, by inhibiting the activation of JNK, and binding to Akt and PKC, triggers dephosphorylation of kinase, and allows protein stabilization, cell survival; similarly, Hsp70 can also bind to DR4 and DR5, and inhibit TRAIL-induced DISC aggregation and activity; (3) DNA degradation pathway: the complex of Hsp70, Hsp40, ICAD can inhibit the activity and folding effect of DNase CAD, prevent late apoptotic chromosomal DNA from being degraded, so as to achieve anti-apoptosis effect.

Study on Hsp70 useful for tumor therapy has become a hot spot in recent years, but a highly active inhibitor has not found yet, and the mechanism of action is not clear. In tumor cells, Hsp70 and its related protein expression are abnormally high. Experiments prove that after dosing stimulation tumor cells play a potential defense mechanism via protein Hsp70 to produce drug resistance, causing a decrease in activity of the drug. Hsp70 inhibitor is expected to reverse the antitumor drug resistance of tumor cell lines.

CONTENTS OF THE INVENTION

The inventors of the present invention design and synthesize a type of Hsp70 inhibitors having novel structure, which can be used for the prevention or treatment of Hsp70-related diseases or conditions, and can effectively reverse drug resistance of bacteria or tumor cells. The present invention is accomplished just based on the above discovery.

In the first aspect, the present invention provides a compound of formula (I), an isomer, a pharmaceutically acceptable salt or a solvate thereof,

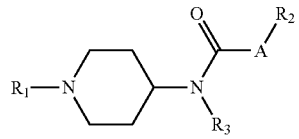

wherein:
A represents $CH_2$, S, O,

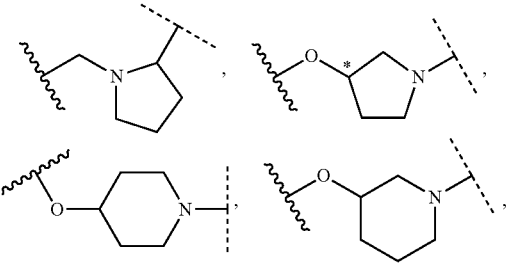

wherein "- - -" terminal is attached to $R_2$;

$R_1$ represents aryl, aromatic heterocyclyl, arylalkyl, or aromatic heterocyclylalkyl, wherein said aryl, aromatic heterocyclyl, arylalkyl, or aromatic heterocyclylalkyl is unsubstituted or substituted with one or two substituents independently selected from the group consisting of halogen, nitro, hydroxy, amino, cyano, alkyl, cycloalkyl, alkoxy, alkylthio, alkylamino, cycloalkoxy, cycloalkylthio, cycloalkylamino, alkenyl and alkynyl;

$R_2$ represents hydrogen, alkyl, cycloalkyl, substituted cycloalkyl, alkoxy, alkoxycarbonyl, alkanoyl, substituted alkanoyl, aliphatic heterocyclyl, substituted aliphatic heterocyclyl, aliphatic heterocyclylalkyl, aryl, substituted aryl, arylalkyl, substituted arylalkyl, arylsulfonyl, substituted arylsulfonyl, arolyl, substituted arolyl, aromatic heterocyclyl, substituted aromatic heterocyclyl, aromatic heterocyclylalkyl, aromatic heterocyclylsulfonyl, aromatic heterocyclylacyl; wherein the substituent includes $C_1$-$C_6$alkyl, halogen, nitro, cyano, amino, hydroxy, alkoxy, mono($C_1$-$C_6$)alkylamino, di($C_1$-$C_6$)alkylamino, $C_2$-$C_6$alkenyl, $C_2$-$C_6$alkynyl, $C_1$-$C_6$haloalkyl, $C_1$-$C_6$haloalkoxy, aromatic heterocyclylalkyl;

$R_3$ represents hydrogen, $C_1$-$C_3$alkyl, or $C_3$-$C_6$cycloalkyl.

The compound of formula (I), an isomer, a pharmaceutically acceptable salt or a solvate thereof according to any item of the first aspect of the present invention is provided, wherein:

$R_1$ represents aromatic heterocyclyl or substituted aromatic heterocyclyl, wherein the substituent is selected from the group consisting of halogen, nitro, amino, cyano, $C_1$-$C_6$alkyl, $C_1$-$C_6$alkoxy, and $C_1$-$C_6$alkylthio.

The compound of formula (I), an isomer, a pharmaceutically acceptable salt or a solvate thereof according to any item of the first aspect of the present invention is provided, wherein:

R$_1$ represents pyrimidinyl or thiazolyl, said pyrimidinyl or thiazolyl being unsubstituted or substituted with one or two substituents independently selected from the group consisting of methyl, halogen, nitro, amino, cyano, methoxy, ethoxy, methylthio and ethylthio.

The compound of formula (I), an isomer, a pharmaceutically acceptable salt or a solvate thereof according to any item of the first aspect of the present invention is provided, wherein:

R$_2$ represents hydrogen, C$_1$-C$_6$alkyl, C$_1$-C$_6$alkoxycarbonyl, C$_1$-C$_6$alkanoyl, substituted C$_1$-C$_6$alkanoyl, 5- or 6-membered aliphatic heterocyclyl, substituted 5- or 6-membered aliphatic heterocyclyl, aryl, substituted aryl, arylC$_1$-C$_6$alkyl, substituted arylC$_1$-C$_6$alkyl, arylsulfonyl, substituted arylsulfonyl, aromatic heterocyclyl, substituted aromatic heterocyclyl, aromatic heterocyclylsulfonyl, aromatic heterocyclylacyl, wherein the substituent is selected from the group consisting of C$_1$-C$_6$alkyl, halogen, nitro, cyano, amino, C$_1$-C$_6$alkoxy, aromatic heterocyclylC$_1$-C$_3$alkyl.

The compound of formula (I), an isomer, a pharmaceutically acceptable salt or a solvate thereof according to any item of the first aspect of the present invention is provided, wherein:

R$_3$ represents hydrogen, or methyl.

The compound of formula (I), an isomer, a pharmaceutically acceptable salt or a solvate thereof according to any item of the first aspect of the present invention is provided, wherein:

A represents CH$_2$, O, S,

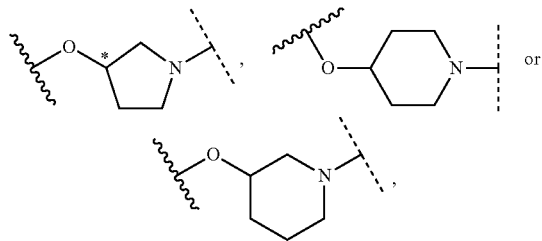

wherein "- - -" terminal is attached to R$_2$;

R$_1$ represents pyrimidinyl, wherein said pyrimidinyl is unsubstituted or substituted with one or two substituents independently selected from the group consisting of methyl, halogen, nitro, amino, cyano, methoxy, ethoxy, methylthio and ethylthio;

R$_2$ represents hydrogen, t-butyl, t-butoxycarbonyl, thiazol-2-sulfonyl, imidazol-1-formyl, phenyl, 1-naphthyl, 2-naphthyl, 4-fluorophenyl, imidazol-1-yl, triazol-1-yl, 2-chloro-benzimidazol-1-yl, 2,3-dichlorobenzenesulfonyl, 2,4-chlorobenzenesulfonyl, 3-chlorobenzyl, 4-chlorobenzyl, 4-fluorobenzyl, acetyl, trifluoroacetyl, 1,2,4-triazol-1-methylpyrrolidin-1-yl;

R$_3$ represents hydrogen, or methyl.

In an embodiment of the present invention, the compound of formula (I), an isomer, a pharmaceutically acceptable salt or a solvate thereof is selected from the following compounds:

(1) t-butyl N-methyl-N-[1-(4-chloropyrimidin-2-yl)piperidin-4-yl]carbamate;
(2) t-butyl N-methyl-N-[1-(2-chloropyrimidin-4-yl)piperidin-4-yl]carbamate;
(3) t-butyl N-methylN-[1-(6-chloropyrimidin-4-yl)piperidin-4-yl]carbamate;
(4) t-butyl N-methyl-N-[1-(4-methoxypyrimidin-2-yl)piperidin-4-yl]carbamate;
(5) t-butyl N-methyl-N-[1-(2-methoxypyrimidin-4-yl)piperidin-4-yl]carbamate;
(6) t-butyl N-methyl-N-[1-(2-methylthiopyrimidin-4-yl)piperidin-4-yl]carbamate;
(7) t-butyl N-methyl-N-[1-(6-methoxypyrimidin-4-yl)piperidin-4-yl]carbamate;
(8) (1-t-butoxycarbonylpiperidin-4-yl) N-methyl-N-[1-(2-methylthiopyrimidin-4-yl) piperidin-4-yl]carbamate;
(9) (S)-(1-t-butoxycarbonylpyrrolidin-3-yl) N-methyl-N-[1-(4-methylthiopyrimidin-2-yl) piperidin-4-yl]carbamate;
(10) (S)-(pyrrolidin-3-yl) N-methyl-N-[1-(2-methylthiopyrimidin-4-yl)piperidin-4-yl]carbamate hydrochloride;
(11) [1-(2,4-dichlorobenzenesulfonyl)piperidin-4-yl] N-methyl-N-[1-(2-methylthiopyrimidin-4-yl)piperidin-4-yl]carbamate;
(12) (S)-[1-(imidazole-1-carbonyl)pyrrolidin-3-yl] N-methyl-N-[1-(2-methylthiopyrimidin-4-yl)piperidin-4-yl]carbamate;
(13) (S)-[1-(2-thienylsulfonyl)pyrrolidin-3-yl] N-methyl-N-[1-(2-methylthiopyrimidin-4-yl) piperidin-4-yl]carbamate;
(14) p-fluorophenylthio N-methyl-N-[1-(2-methoxypyrimidin-4-yl)piperidin-4-yl]carbamate;
(15) p-fluorophenylthio N-methyl-N-[1-(2-methylthiopyrimidin-4-yl)piperidin-4-yl]carbamate;
(16) (1-acetylpiperidin-4-yl) N-methyl-N-[1-(4-methoxypyrimidin-2-yl)piperidin-4-yl]carbamate;
(17) (S)-[1-(2-thienylsulfonyl)pyrrolidin-3-yl] N-methyl-N-[1-(4-methoxypyrimidin-2-yl) piperidin-4-yl]carbamate;
(18) [1-(3-chlorobenzyl)piperidin-3-yl] N-methyl-N-[1-(2-methoxypyrimidin-4-yl) piperidin-4-yl]carbamate;
(19) [1-(3-chlorobenzyl)piperidin-4-yl] N-methyl-N-[1-(4-methoxypyrimidin-2-yl) piperidin-4-yl]carbamate;
(20) [1-(2,3-dichlorobenzenesulfonyl)piperidin-3-yl] N-methyl-N-[1-(2-methoxypyrimidin-4-yl)piperidin-4-yl]carbamate;
(21) [1-(2,4-dichlorobenzenesulfonyl)piperidin-4-yl] N-methyl-N-[1-(4-methoxypyrimidin-2-yl)piperidin-4-yl]carbamate;
(22) [1-(4-fluorobenzyl)piperidin-3-yl] N-methyl-N-[1-(2-methoxypyrimidin-4-yl) piperidin-4-yl]carbamate;
(23) (S)-[1-(2,3-dichlorobenzenesulfonyl)pyrrolidin-3-yl] N-methyl-N-[1-(2-methylthiopyrimidin-4-yl)piperidin-4-yl]carbamate;
(24) (S)-[1-(2,4-dichlorobenzenesulfonyl)pyrrolidin-3-yl] N-methyl-N-[1-(2-methylthiopyrimidin-4-yl)piperidin-4-yl]carbamate;
(25) (1-acetylpiperidin-3-yl) N-methyl-N-[1-(6-methoxypyrimidin-4-yl)piperidin-4-yl]carbamate;
(26) [1-(2,2,2-trifluoroacetyl)piperidin-3-yl] N-methyl-N-[1-(6-methoxypyrimidin-4-yl) piperidin-4-yl]carbamate;
(27) [1-(imidazole-1-carbonyl)piperidin-3-yl] N-methyl-N-[1-(6-methoxypyrimidin-4-yl) piperidin-4-yl]carbamate;
(28) [1-(2-thienylsulfonyl)piperidin-3-yl] N-methyl-N-[1-(2-methoxypyrimidin-4-yl) piperidin-4-yl]carbamate;
(29) [1-(1-thienylsulfonyl)piperidin-4-yl] N-methyl-N-[1-(4-methoxypyrimidin-2-yl) piperidin-4-yl]carbamate;
(30) N-methyl-N-[1-(4-chloropyrimidin-2-yl)piperidin-4-yl]-[2-(imidazol-1-yl)]acetamide;
(31) N-methyl-N-[1-(4-chloropyrimidin-2-yl)piperidin-4-yl]-2-(1H-1,2,4-triazol-1-yl) acetamide;
(32) N-methyl-N-[1-(2-methoxypyrimidin-4-yl)piperidin-4-yl]-2-(2-chloro-benzoimidazol-1-yl)acetamide;
(33) N-methyl-N-[1-(6-methoxypyrimidin-4-yl)piperidin-4-yl]-[2-(imidazol-1-yl)]acetamide;

(34) N-methyl-N-[1-(6-methoxypyrimidin-4-yl)piperidin-4-yl]-2-(1H-1,2,4-triazol-1-yl) acetamide;
(35) N-methyl-N-[1-(6-methoxypyrimidin-4-yl)piperidin-4-yl]-2-(2-chloro-benzoimidazol-1-yl)acetamide;
(36) N-methyl-N-[1-(2-methylthiopyrimidin-4-yl)piperidin-4-yl]-2-{[3-(1H-1,2,4-triazol-1-methyl)]pyrrolidin-1-yl}acetamide;
(37) N-methyl-N-[1-(2-methoxypyrimidin-4-yl)piperidin-4-yl]-2-{[2-(1H-1,2,4-triazol-1-methyl)]pyrrolidin-1-yl}acetamide;
(38) N-methyl-N-[1-(6-methoxypyrimidin-4-yl)piperidin-4-yl]-2-{[2-(1H-1,2,4-triazol-1-methyl)]pyrrolidin-1-yl}acetamide;
(39) N-methyl-N-[1-(4-methoxypyrimidin-2-yl)piperidin-4-yl]-2-{[2-(1H-1,2,4-triazol-1-methyl)]pyrrolidin-1-yl}acetamide;
(40) N-methyl-N-[1-(6-methoxypyrimidin-4-yl)piperidin-4-yl]-2-(1H-1,2,4-triazol-1-yl) acetamide;
(41) N-methyl-N-[1-(4-methylpyrimidin-2-yl)piperidin-4-yl]-2-(2-chloro-benzoimidazol-1-yl) acetamide;
(42) N-methyl-N-[1-(4-methoxypyrimidin-2-yl)piperidin-4-yl]-2-(1H-1,2,4-triazol-1-yl) acetamide;
(43) N-methyl-N-[1-(2-methoxypyrimidin-4-yl)piperidin-4-yl]-2-(1H-1,2,4-triazol-1-yl) acetamide;
(44) N-methyl-N-[1-(2-methylthiopyrimidin-4-yl)piperidin-4-yl]-2-(1H-1,2,4-triazol-1-yl) acetamide.

In the second aspect, the present invention provides a method for preparing the compound of formula (I), an isomer, a pharmaceutically acceptable salt or a solvate thereof according to any item of the first aspect of the present invention, which comprises the following steps:

(1) Compound 2 and compound 1 undergo nucleophilic substitution reaction to obtain compound 3; compound 3 is attacked by nucleophilic agent Nu⁻ to obtain compound 4; compound 4 undergoes amino deprotection and amidation reaction respectively to obtain an active intermediate 6; wherein, in compound 1, A, B, C represent C or N atom, and at least one of them is C atom; L is a conventional leaving group such as halogen, —OCOR, —OTs, etc., two Ls may be the same or different, preferably in meta or para arrangement; Pg is an amino protective group such as Boc; $R_1$ and $R_3$ are as defined in claim 1; compound 6 is an amidation product of compound 5, for example, reaction product of compound 5 with chloroacetyl chloride, carbonyl diimidazole or triphosgene, etc.; according to different amidation reagent, compound 6 may be respectively the following three forms 6-1, 6-2 or 6-3;

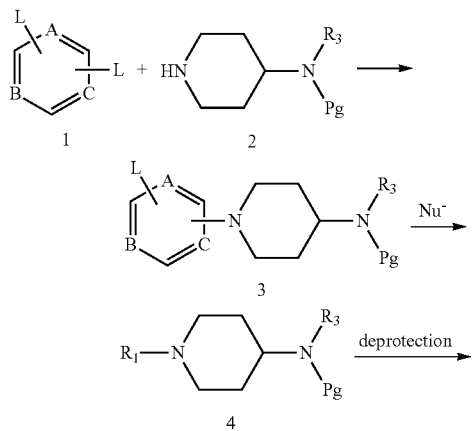

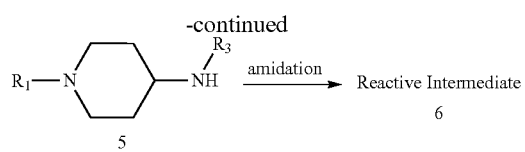

(2) According to different definition of A, the compound of formula (I) as claimed in claim 1 can be prepared by the following steps respectively:

When A is $CH_2$, $R_2H$ is nucleophilic agent, such as amine; $R_2H$ and compound 6-1 directly undergo nucleophilic substitution reaction to obtain compound I-1; wherein $R_1$, $R_2$, $R_3$ are as defined in claim 1;

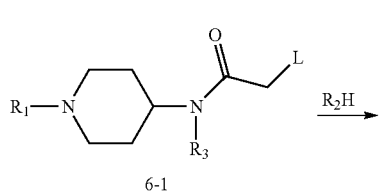

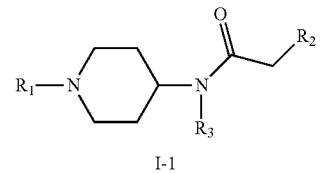

When A is S, $R_2SH$ is nucleophilic agent, such as thiophenol, $R_2SH$ and compound 6-2 directly undergo nucleophilic substitution reaction to obtain compound 1-2; wherein $R_1$, $R_2$, $R_3$ are as defined in claim 1; L is a conventional leaving group, such as halogen;

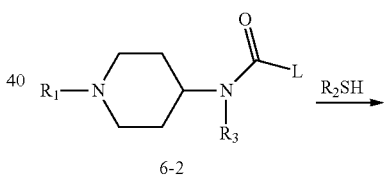

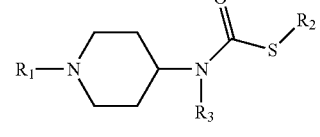

When A is

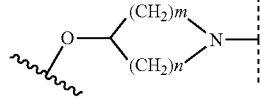

m=1, 2, n=2, 3; and when m=1, n=2 or 3; and when m=2, n=2; compound 6-3 and compound 9 undergo nucleophilic addition reaction to obtain compound 7; compound 7 undergoes amino deprotection to obtain compound 8; finally, compound 8 and $R_2L$ undergo nucleophilic substitution reaction to obtain compound 1-3; wherein $R_1$, $R_2$, $R_3$ are as defined in claim 1; Pg is a conventional amino protective group, such as Boc;

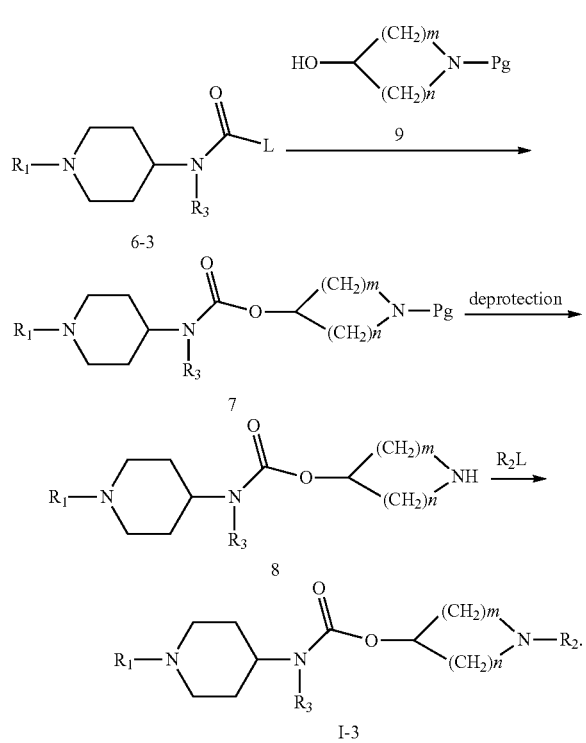

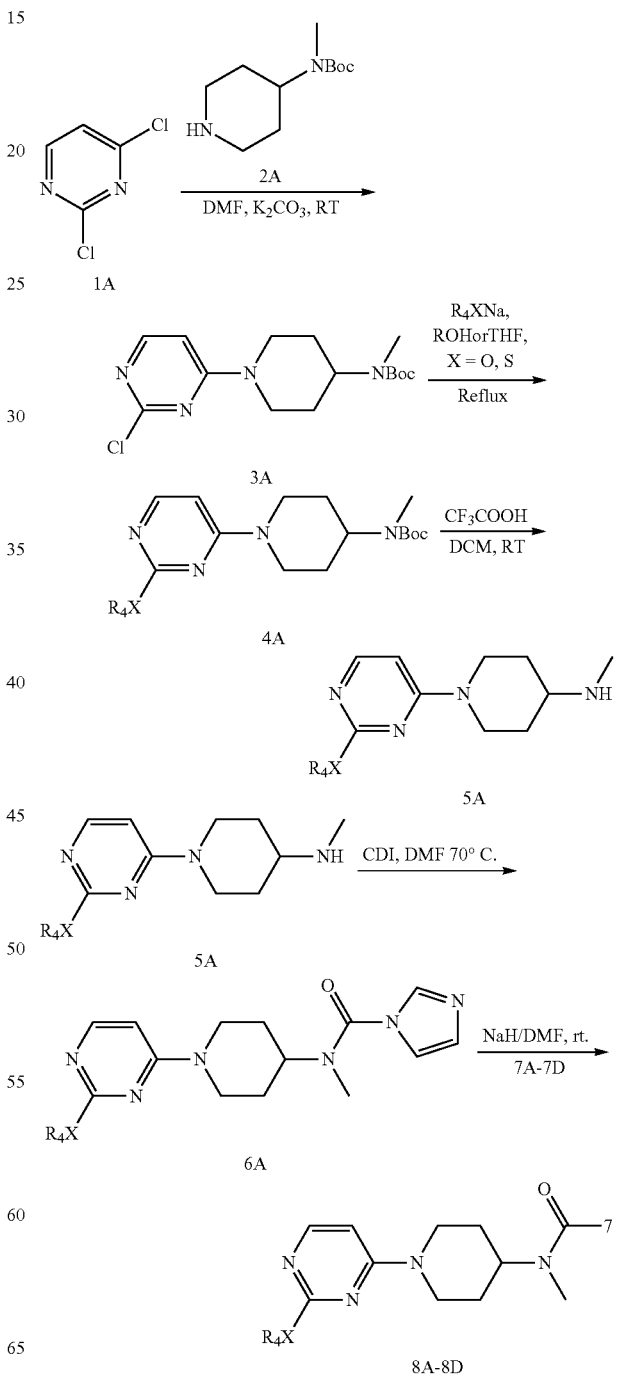

The above compounds 3, 4, 5, 7, 8, 9, I-1, I-2 and I-3 are all within the scope of the formula (I), and all fall into the protection scope of the present invention.

Nucleophilic reagent refers to a reagent having nucleophilicity, such as compounds having hydroxy, thiol, amino and the like.

Pg is a conventional amino protective group. As to concrete protection and deprotection methods, please refer to, Green and Woods, Protective Groups in Organic Synthesis, Chapter 7 "Protection of amino group".

The preparation method according to the second aspect of the present invention, when $R_1$ is a pyrimidine ring, comprises the following reaction route, i.e., first, 2,4-dichloro-pyrimidine or 4,6-dichloro-pyrimidine as starting material reacts with t-butyl N-methyl-N-(piperidin-4-yl)carbamate in a solvent such as THF or DMF, at normal temperature, in the presence of potassium carbonate, sodium carbonate or sodium bicarbonate, to obtain compound 3A; compound 3A then reacts with sodium methoxide, sodium ethoxide or sodium thiomethoxide in the corresponding alcohol or THF solvent under refluxing conditions to obtain compound 4A; compound 4A undergoes BOC removal under the action of trifluoroacetic acid in DCM solvent at room temperature to obtain intermediate 5A; intermediate 5A reacts with CDI in DMF under heating conditions to obtain compound 6A; compound 6A and the corresponding alcohol dissolved in DMF or DMSO react with compounds 7A-7D respectively at room temperature under the catalysis of NaH to obtain compounds 8A-8D; compounds 8B, 8C, 8D respectively undergo deprotection under the action of trifluoroacetic acid in DCM at room temperature to obtain compounds 9B, 9C, 9D; compounds 9B, 9C, 9D respectively undergo condensation reaction with the corresponding sulfonyl chloride 11 (1) or acid chloride (2) in a solvent such as THF or DMF at room temperature, while neutralizing acid generated during the reaction using potassium carbonate, sodium carbonate, sodium bicarbonate, to obtain compounds 10(1)B-10(1)D and 10(2)B-10(2)D of the present invention; or Intermediate 5A dissolved in DCM undergoes condensation reaction with 2-chloroacetyl chloride in an ice bath, while neutralizing acid generated during the reaction using TEA and the like, to obtain compound 12A; compound 12A then reacts with the corresponding amine in a solvent such as DMF or THF at room temperature, in the presence of potassium carbonate, sodium carbonate or sodium bicarbonate, to obtain compound 13A of the present invention;

The product can be separated and purified using standard techniques in the art, such as extraction, chromatography, crystallization and distillation.

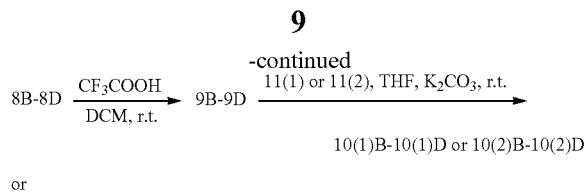
or
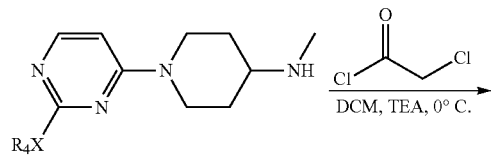
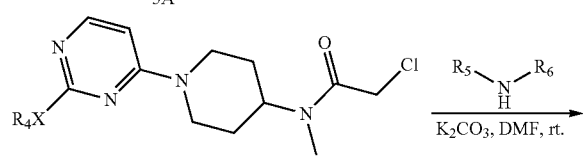
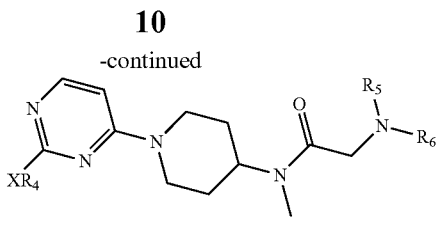
wherein, compounds 11 (1) and 11 (2) mentioned in the above formula are respectively:
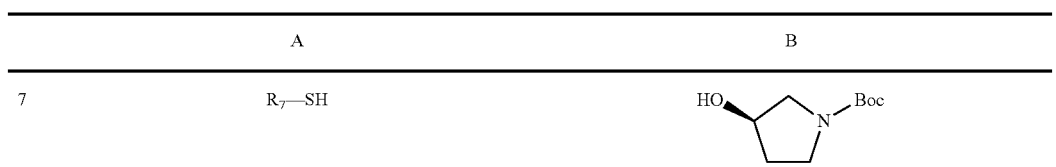
7A-7D, 8B-8D, 9B-9D, 10 (1)B-10 (1)D and 10 (2)B-10 (2)D are respectively:
| | A | B |
|---|---|---|
| 7 | R$_7$—SH | 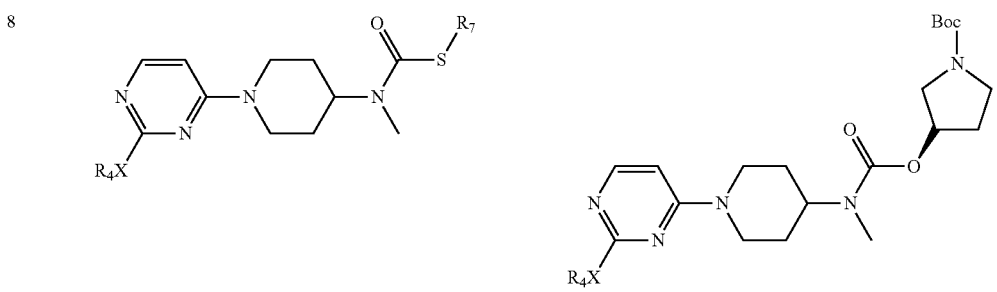 |
| 8 | | |
| 9 | | 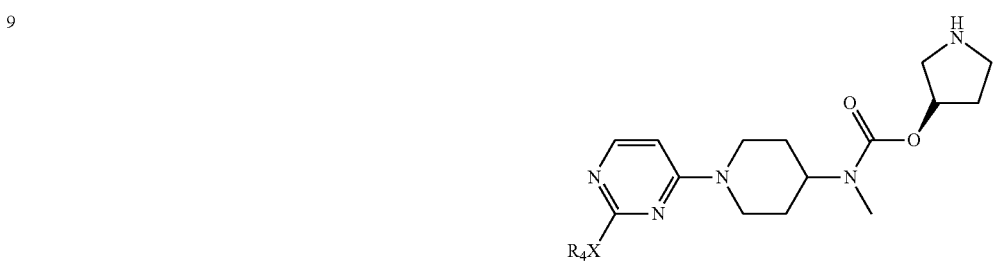 |
| 10 (1) | | 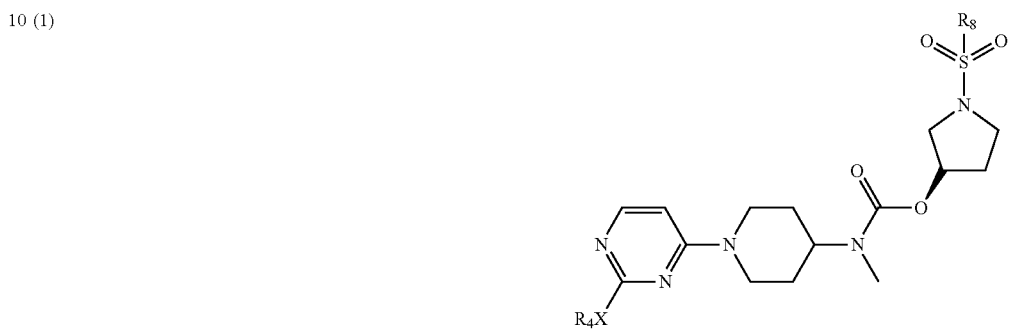 |

-continued
| | C | D |
|---|---|---|
| 10 (2) | | 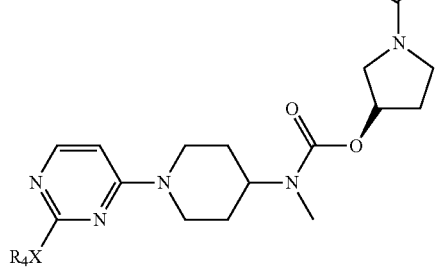 |
| 7 | 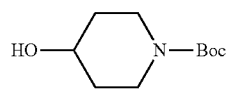 | 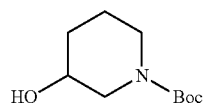 |
| 8 | 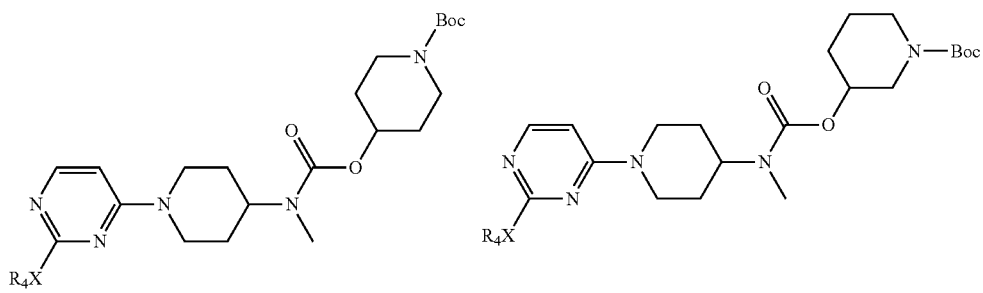 | |
| 9 | 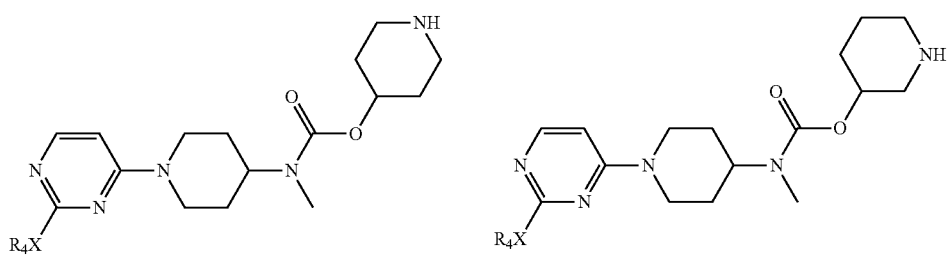 | |
| 10 (1) | 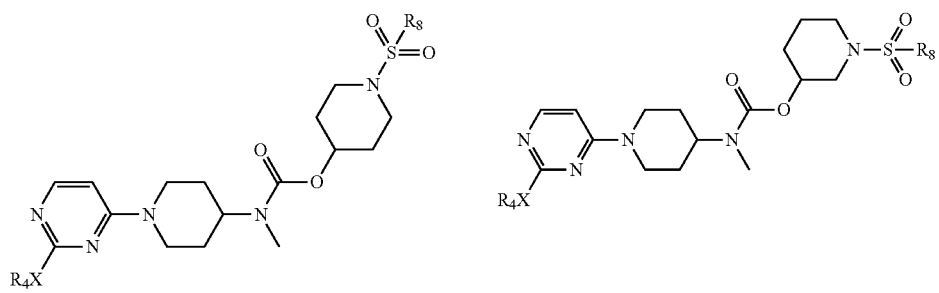 | |
| 10 (2) | 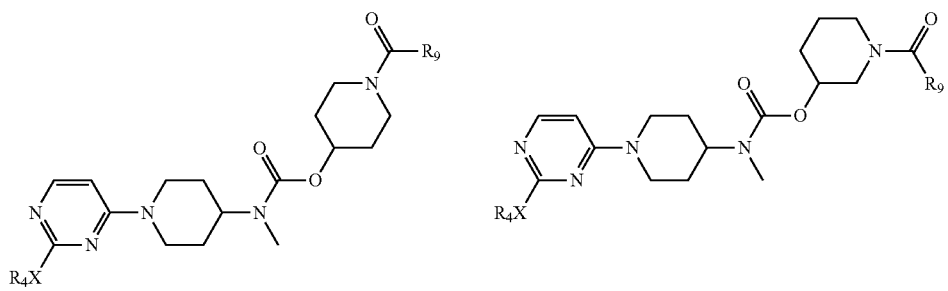 | |

In the third aspect, the present invention provides a pharmaceutical composition comprising the compound of formula (I), an isomer, a pharmaceutically acceptable salt or a solvate thereof according to any item of the first aspect of the present invention, and a pharmaceutically acceptable carrier or excipient.

The pharmaceutical composition according to any item of the third aspect of the present invention further comprises one or more of other antitumor drugs, for example, tinib-based antitumor drugs, such as gefitinib, imatinib, imatinib mesylate, nilotinib, sunitinib, lapatinib.

In the fourth aspect, the present invention provides use of the compound of formula (I), an isomer, a pharmaceutically acceptable salt or a solvate thereof according to any item of the first aspect of the present invention in the manufacture of a drug for preventing and/or treating drug-resistant tumors or diseases or conditions caused by drug-resistant bacteria.

In the fifth aspect, the present invention provides use of the compound of formula (I), an isomer, a pharmaceutically acceptable salt or a solvate thereof according to any item of the first aspect of the present invention in the manufacture of a drug for preventing and/or treating tumors, neurodegenerative diseases, allograft rejection, and diseases or conditions related to infection. Preferably, the tumors, neurodegenerative diseases, allograft rejection, and diseases or conditions related to infection are diseases or conditions caused by Heat shock protein 70 (Hsp70).

In the use according to any item of the fourth or fifth aspect of the present invention, the tumors are selected from the group consisting of breast cancer, prostate cancer, liver cancer, esophageal cancer, gastric cancer, and skin cancer.

In the use according to any item of the fifth aspect of the present invention, the neurodegenerative diseases are selected from the group consisting of Alzheimer's disease, amyotrophic lateral sclerosis, ataxia telangiectasia, Creutzfeldt-Jakob disease, Huntington's disease, cerebellar atrophy, multiple sclerosis, Parkinson's disease, primary lateral sclerosis, and spinal muscular atrophy.

In the sixth aspect, the present invention provides a method for preventing and/or treating drug-resistant tumors or diseases or conditions caused by drug-resistant bacteria, which comprises administering to a subject in need of such prevention or treatment a prophylactically and/or therapeutically effective amount of the compound of formula (I), an isomer, a pharmaceutically acceptable salt or a solvate thereof according to any item of the first aspect of the present invention.

In the seventh aspect, the present invention provides a method for preventing and/or treating tumors, neurodegenerative diseases, allograft rejection, and diseases or conditions related to infection, which comprises administering to a subject in need of such prevention or treatment a prophylactically and/or therapeutically effective amount of the compound of formula (I), an isomer, a pharmaceutically acceptable salt or a solvate thereof according to any item of the first aspect of the present invention. Preferably, the tumors, neurodegenerative diseases, allograft rejection, and diseases or conditions related to infection are diseases or conditions caused by Heat shock protein 70 (Hsp70).

In the method according to any item of the sixth or seventh aspect of the present invention, the tumors are selected from the group consisting of breast cancer, prostate cancer, liver cancer, esophageal cancer, gastric cancer, and skin cancer.

In the method according to any item of the seventh aspect of the present invention, the neurodegenerative diseases are selected from the group consisting of Alzheimer's disease, amyotrophic lateral sclerosis, ataxia telangiectasia, Creutzfeldt-Jakob disease, Huntington's disease, cerebellar atrophy, multiple sclerosis, Parkinson's disease, primary lateral sclerosis, and spinal muscular atrophy.

In the eighth aspect, the present invention provides the compound of formula (I), an isomer, a pharmaceutically acceptable salt or a solvate thereof according to any item of the first aspect of the present invention, for preventing and/or treating drug-resistant tumors or diseases caused by drug-resistant bacteria.

In the ninth aspect, the present invention provides the compound of formula (I), an isomer, a pharmaceutically acceptable salt or a solvate thereof according to any item of the first aspect of the present invention, for preventing and/or treating tumors, neurodegenerative diseases, allograft rejection, and diseases or conditions related to infection. Preferably, the tumors, neurodegenerative diseases, allograft rejection, and diseases or conditions related to infection are diseases or conditions caused by Heat shock protein 70 (Hsp70).

The compound of formula (I), an isomer, a pharmaceutically acceptable salt or a solvate thereof according to any item of the eighth or ninth aspect of the present invention, wherein the tumors are selected from the group consisting of breast cancer, prostate cancer, liver cancer, esophageal cancer, gastric cancer, and skin cancer.

The compound of formula (I), an isomer, a pharmaceutically acceptable salt or a solvate thereof according to any item of the ninth aspect of the present invention, wherein the neurodegenerative diseases are selected from the group consisting of Alzheimer's disease, amyotrophic lateral sclerosis, ataxia telangiectasia, Creutzfeldt-Jakob disease, Huntington's disease, cerebellar atrophy, multiple sclerosis, Parkinson's disease, primary lateral sclerosis, and spinal muscular atrophy.

In the tenth aspect, the present invention provides a method for resisting/reversing drug resistance of bacteria or drug resistance of tumor cells in cells, which comprises administering to the cells an effective amount of the compound of formula (I), an isomer, a pharmaceutically acceptable salt or a solvate thereof according to any item of the first aspect of the present invention.

In the eleventh aspect, the present invention provides a method for inhibiting expression of Heat shock protein 70 (Hsp70) in cells, which comprises administering to the cells an effective amount of the compound of formula (I), an isomer, a pharmaceutically acceptable salt or a solvate thereof according to any item of the first aspect of the present invention.

In the method according to any item of the tenth or eleventh aspect of the present invention, the cells are cell lines, or cells from a subject.

In the method according to any item of the tenth or eleventh aspect of the present invention, the tumor cells are selected from the group consisting of breast cancer cells, prostate cancer cells, liver cancer cells, esophageal cancer cells, gastric cancer cells, and skin cancer cells.

In the method according to any item of the tenth or eleventh aspect of the present invention, wherein the method is carried out in vitro.

In the method according to any item of the tenth or eleventh aspect of the present invention, wherein the method is carried out in vivo.

In the twelfth aspect, the present invention provides use of the compound of formula (I), an isomer, a pharmaceutically acceptable salt or a solvate thereof according to any item of the first aspect of the present invention in the manufacture of a reagent for resisting/reversing drug resistance of bacteria or drug resistance of tumor cells in cells.

In the thirteenth aspect, the present invention provides use of the compound of formula (I), an isomer, a pharmaceutically acceptable salt or a solvate thereof according to any item of the first aspect of the present invention in the manufacture of a reagent for inhibiting activity of Heat shock protein 70 (Hsp70) in cells.

In the use according to any item of the twelfth or thirteenth aspect of the present invention, the cells are cell lines, or cells from a subject.

In the use according to any item of the twelfth or thirteenth aspect of the present invention, the tumor cells are selected from the group consisting of breast cancer cells, prostate cancer cells, liver cancer cells, esophageal cancer cells, gastric cancer cells, and skin cancer cells.

In the use according to any item of the twelfth or thirteenth aspect of the present invention, the reagent is used in an in vitro method.

In the use according to any item of the twelfth or thirteenth aspect of the present invention, the reagent is used in an in vivo method.

In the fourteenth aspect, the present invention provides the compound of formula (I), an isomer, a pharmaceutically acceptable salt or a solvate thereof according to any item of the first aspect of the present invention, for resisting/reversing drug resistance of bacteria or drug resistance of tumor cells in cells.

In the fifteenth aspect, the present invention provides the compound of formula (I), an isomer, a pharmaceutically acceptable salt or a solvate thereof according to any item of the first aspect of the present invention, for inhibiting activity of Heat shock protein 70 (Hsp70) in cells.

The compound of formula (I), an isomer, a pharmaceutically acceptable salt or a solvate thereof according to any item of the fourteenth or fifteenth aspect of the present invention, wherein the cells are cell lines, or cells from a subject.

The compound of formula (I), an isomer, a pharmaceutically acceptable salt or a solvate thereof according to any item of the fourteenth or fifteenth aspect of the present invention, wherein the tumor cells are selected from the group consisting of breast cancer cells, prostate cancer cells, liver cancer cells, esophageal cancer cells, gastric cancer cells, and skin cancer cells.

The compound of formula (I), an isomer, a pharmaceutically acceptable salt or a solvate thereof according to any item of the fourteenth or fifteenth aspect of the present invention, which is used in an in vitro method.

The compound of formula (I), an isomer, a pharmaceutically acceptable salt or a solvate thereof according to any item of the fourteenth or fifteenth aspect of the present invention, which is used in an in vivo method.

In the sixteenth aspect, the present invention provides a kit for resisting/reversing drug resistance of bacteria or drug resistance of tumor cells in cells, which comprises the compound of formula (I), an isomer, a pharmaceutically acceptable salt or a solvate thereof according to any item of the first aspect of the present invention, and optionally instructions.

In the seventeenth aspect, the present invention provides a kit for inhibiting activity of Heat shock protein 70 (Hsp70) in cells, which comprises the compound of formula (I), an isomer, a pharmaceutically acceptable salt or a solvate thereof according to any item of the first aspect of the present invention, and optionally instructions.

The terms for describing the present invention occurred in the present specification and claims are defined as follows. As to specific terms, if the meanings thereof defined in the present application are inconsistent with the meanings thereof commonly understood by a person skilled in the art, they have the meanings defined in the present application; if not defined in the present application, the terms have the meanings commonly understood by a person skilled in the art.

The term "alkyl" used herein refers to straight or branched chain monovalent saturated hydrocarbon group, for example, $C_1$-$C_{10}$alkyl, $C_1$-$C_6$alkyl, $C_1$-$C_3$alkyl. The term "$C_1$-$C_{10}$alkyl" refers to straight or branched chain alkyl having 1 to 10 carbon atoms, e.g., methyl, ethyl, propyl, isopropyl, n-butyl, s-butyl, t-butyl, isobutyl, pentyl, 2-pentyl, isopentyl, neopentyl, hexyl, 2-hexyl, 3-hexyl, 3-methylpentyl, heptyl and octyl and the like. The term "$C_1$-$C_6$alkyl" refers to straight or branched chain alkyl having 1 to 6, i.e., 1, 2, 3, 4, 5 or 6, carbon atoms, typically methyl, ethyl, n-propyl, isopropyl, n-butyl, isobutyl, t-butyl, pentyl and hexyl and the like. The term "$C_1$-$C_3$alkyl" refers to straight or branched chain alkyl having 1, 2 or 3 carbon atoms, i.e. methyl, ethyl, n-propyl and isopropyl. In the present invention, alkyl is preferably $C_{1-6}$ alkyl.

The term "$C_2$-$C_6$alkenyl" used herein refers to alkenyl having 2 to 6 carbon atoms. The alkenyl has 1, 2 or 3 carbon-carbon double bonds. When there is more than one carbon-carbon double bond, the carbon-carbon double bonds are conjugated or non-conjugated. Examples of $C_2$-$C_6$alkenyl in the present invention include vinyl, propenyl.

The term "$C_2$-$C_6$alkynyl" used herein refers to alkynyl having 2 to 6 carbon atoms. The alkynyl has 1, 2 or 3 carbon-carbon triple bonds. When there is more than one carbon-carbon triple bond, the carbon-carbon triple bonds are conjugated or non-conjugated. Examples of $C_2$-$C_6$alkynyl in the present invention include ethynyl, propynyl.

The term "halogen" used herein refers to fluorine, chlorine, bromine and iodine atoms.

The term "aryl" used herein refers to an optionally substituted monocyclic or bicyclic unsaturated aromatic system having at least one unsaturated aromatic ring, preferably aryl having 6 to 10, i.e., 6, 7, 8, 9 or 10 carbon atoms. Examples of aryl in the present invention include phenyl, naphthyl, 1,2,3,4-tetrahydronaphthyl and indenyl and the like. In the present invention, aryl may be substituted with the following groups: $C_1$-$C_6$alkyl, $C_1$-$C_6$alkoxy, cyano, halo, hydroxy, amino, nitro, mono($C_1$-$C_6$)alkylamino, di($C_1$-$C_6$) alkylamino, $C_2$-$C_6$alkenyl, $C_2$-$C_6$alkynyl, $C_1$-$C_6$haloalkyl or $C_1$-$C_6$haloalkoxy. Specific examples include, but are not limited to, 4-fluorophenyl.

Wherein, "alkyl" as defined above is substituted with one or more of the aryl as defined above, or sulfonyl, acyl are respectively substituted with the aryl as defined above, to obtain the aforesaid "arylalkyl", "arylsulfonyl", "arolyl" respectively.

Wherein, "alkyl" as defined above is substituted with one or more of the substituted aryl as defined above, or sulfonyl, acyl are respectively substituted with the substituted aryl as defined above, to obtain the aforesaid "substituted arylalkyl", "substituted arylsulfonyl", "substituted arolyl" respectively. Wherein, the arylalkyl is, for example, aryl$C_1$-$C_3$ alkyl.

In the present invention, specific examples of the "arylalkyl", "arylsulfonyl", "arolyl", "substituted arylalkyl", "substituted arylsulfonyl" or "substituted arolyl" include, but are not limited to, benzyl, phenethyl, 3-chlorobenzyl, 4-chlorobenzyl, 4-fluorobenzyl, 2,3-dichlorobenzenesulfonyl, 2,4-dichlorobenzenesulfonyl.

The term "aromatic heterocyclyl" used herein refers to an optionally substituted monocyclic or bicyclic unsaturated aromatic ring system containing at least one, for example, 1, 2, 3 or 4 heteroatoms independently selected from N, O or S, preferably aromatic heterocyclyl having 5 to 10, i.e., 5, 6, 7, 8, 9 or 10 ring atoms. Examples of the "aromatic heterocyclyl" include, but are not limited to, thienyl, pyridyl, thiazolyl, isothiazolyl, furanyl, pyrrolyl, triazolyl, imidazolyl, triazinyl, diazolyl, oxazolyl, isoxazolyl, pyrazolyl, imidazolonyl, oxazolyl, thiazolonyl, tetrazolyl, thiadiazolyl, benzimidazolyl, benzoxazolyl, benzothiazolyl, tetrahydrotriazolopyridyl, tetrahydrotriazolopyrimidinyl, benzofuranyl, benzothienyl, thioindenyl, indolyl, isoindolyl, pyridonyl, pyridazinyl, pyrazinyl, pyrimidinyl, quinolinyl, phthalazinyl, quinoxalinyl, quinazolinyl, imidazopyridyl, oxazolopyridyl, thiazolopyridyl, imidazopyridazinyl, oxazolopyridazinyl, thiazolopyridazinyl, pteridinyl, furazanyl, benzotriazolyl, pyrazolopyridyl and purinyl and the like.

The term "aliphatic heterocyclyl" used herein refers to an optionally substituted monocyclic or bicyclic saturated or partially saturated ring system containing at least one and up to four, for example, 1, 2, 3 or 4 heteroatom independently selected from N, O or S, preferably aliphatic heterocyclyl having 4 to 10, i.e., 4, 5, 6, 7, 8, 9 or 10 ring atoms, with the proviso that the ring of the heterocyclyl does not contain two adjacent O or S atoms. Preferred aliphatic heterocyclyl includes, but is not limited to, saturated cycloalkyl containing at least one, for example, 1, 2 or 3 heteroatom independently selected from N, O or S, preferably aliphatic heterocyclyl having 3 to 8, i.e., 3, 4, 5, 6, 7 or 8 ring atoms. Examples of the "aliphatic heterocyclyl" include, but are not limited to, pyrrolidinyl, tetrahydrofuranyl, dihydrofuranyl, tetrahydrothienyl, piperidinyl, morpholinyl or piperazinyl and the like.

In the present invention, aromatic heterocyclyl or aliphatic heterocyclyl may be substituted with the following groups: $C_1$-$C_6$alkyl, $C_1$-$C_6$alkoxy, cyano, halogen, hydroxy, amino, nitro, mono($C_1$-$C_6$)alkylamino, di($C_1$-$C_6$)alkylamino, $C_2$-$C_6$alkenyl, $C_2$-$C_6$alkynyl, $C_1$-$C_6$haloalkyl, $C_1$-$C_6$haloalkoxy or aromatic heterocyclylalkyl or substituted aromatic heterocyclylalkyl, to obtain the aforesaid "substituted aromatic heterocyclyl" or "substituted aliphatic heterocyclyl". Specific examples include, but are not limited to, 2-chloropyrimidin-4-yl, 4-chloropyrimidin-2-yl, 6-chloropyrimidin-4-yl, 2-methoxypyrimidin-4-yl, 4-methoxypyrimidin-2-yl, 6-methoxypyrimidin-4-yl, 2-methylthiopyrimidin-4-yl, 4-methylthiopyrimidin-2-yl, 6-methylthiopyrimidin-4-yl, 1,2,4-triazol-1-methyl, 2-methylpyrimidin-4-yl, 4-methylpyrimidin-2-yl, 6-methylpyrimidin-4-yl, 2-chlorobenzoimidazol-1-yl, tetrahydropyranylmethyl.

Wherein, "alkyl" as defined above is substituted with one or more of the aromatic heterocyclyl as defined above, or sulfonyl, acyl are respectively substituted with the aromatic heterocyclyl as defined above, to obtain the aforesaid "aromatic heterocyclylalkyl", "aromatic heterocyclylsulfonyl", "aromatic heterocyclylacyl" respectively.

When "alkyl" as defined above is substituted with one or more of the substituted aromatic heterocyclyl as defined above, or sulfonyl, acyl are respectively substituted with the substituted aromatic heterocyclyl as defined above, to obtain the aforesaid "substituted aromatic heterocyclylalkyl", "substituted aromatic heterocyclylsulfonyl", "substituted aromatic heterocyclylacyl" respectively. Wherein, the aromatic heterocyclylalkyl is, for example, 5- or 6-membered aromatic heterocyclyl$C_1$-$C_3$ alkyl.

In the present invention, specific examples of the "aromatic heterocyclylalkyl", "aromatic heterocyclylsulfonyl", "aromatic heterocyclylacyl", "substituted aromatic heterocyclylalkyl", "substituted aromatic heterocyclylsulfonyl" or "substituted aromatic heterocyclylacyl" include, but are not limited to, pyridylethyl, imidazol-1-formyl, thiazol-2-sulfonyl.

The term "$C_3$-$C_6$cycloalkyl" used herein refers to a saturated carbocyclic group having 3 to 6, i.e., 3, 4, 5 or 6 carbon atoms. The cycloalkyl may be monocyclic or polycyclic fused system, and can be fused to an aromatic ring. Examples of such groups include cyclopropyl, cyclobutyl, cyclopentyl and cyclohexyl and the like. Cycloalkyl herein may be unsubstituted or substituted with appropriate group at one or more substitutable positions. For example, in the present invention, the cycloalkyl can be optionally substituted with the following groups: $C_1$-$C_6$alkyl, $C_1$-$C_6$alkoxy, cyano, halogen, hydroxy, amino, nitro, mono($C_1$-$C_6$)alkylamino, di($C_1$-$C_6$)alkylamino, $C_2$-$C_6$alkenyl, $C_2$-$C_6$alkynyl, $C_1$-$C_6$haloalkyl or $C_1$-$C_6$haloalkoxy.

The term "pharmaceutically acceptable salts" used herein refers to salts of compounds of the present invention which are pharmaceutically acceptable and have the desired pharmacological activity of the parent compounds. The salts include: acid addition salts formed with inorganic acids or organic acids, wherein the inorganic acids are such as hydrochloric acid, hydrobromic acid, sulfuric acid, nitric acid, phosphoric acid and the like; and the organic acids are such as acetic acid, propionic acid, hexanoic acid, cyclopentyl propionic acid, glycolic acid, pyruvic acid, lactic acid, malonic acid, succinic acid, malic acid, maleic acid, fumaric acid, tartaric acid, citric acid, benzoic acid, cinnamic acid, mandelic acid, methanesulfonic acid, ethanesulfonic acid, benzenesulfonic acid, naphthalene sulfonic acid, camphor sulfonic acid, glucoheptonic acid, gluconic acid, glutamic acid, hydroxynaphthoic acid, salicylic acid, stearic acid, muconic acid and the like; or salts formed when acidic protons present on the parent compounds are substituted with metal ions, such as alkali metal ions or alkaline earth metal ions; or coordination compounds formed with organic base, wherein the organic base is such as ethanolamine, diethanolamine, triethanolamine, N-methyl glucosamine and the like.

The term "solvate" used herein refers to a substance formed by combining the compound of the present invention with a pharmaceutically acceptable solvent. The pharmaceutically acceptable solvent includes water, ethanol, acetic acid and the like. The solvate includes stoichiometric amount of solvate and non-stoichiometric amount of solvate, and is preferably hydrate. The compound of the present invention may be crystallized or recrystallized with water or various organic solvents. In this case, various solvates may be formed.

The term "subject" used herein includes mammals and human, preferably human.

Those skilled in the art will appreciate that the compound of the invention has stereoisomerism, for example, cis- and trans-isomers or enantiomers. Therefore, when the compound of the present invention is mentioned in the present specification, the compound of the present invention includes a compound of formula (I), an isomer, a pharmaceutically acceptable salt or a solvate thereof. The compound of the present invention also includes active metabolite of the compound of the present invention in mammals.

The present specification illustrates in the part "Mode of carrying out the invention" the preparation method of the compound of the present invention and the anti-tumor effect of the same.

The pharmaceutical composition of the present invention comprises an effective amount of the compound of formula (I), an isomer, a pharmaceutically acceptable salt or a solvate thereof, and one or more pharmaceutically acceptable carrier. The pharmaceutically acceptable carrier herein includes, but is not limited to: ion exchangers, alumina, aluminum stearate, lecithin, serum proteins such as human serum albumin, buffers such as phosphates, glycerine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinylpyrrolidone, cellulose-based materials, polyethylene glycol, sodium carboxymethylcellulose, polyacrylate, beeswax, lanolin.

The pharmaceutical composition comprising the compound of the present invention can be administered according to any of the following routes: oral, spray inhalation, rectal, nasal, buccal, topical, parenteral such as subcutaneous, intravenous, intramuscular, intraperitoneal, intrathecal, intraventricular, intrasternal or intracranial injection or infusion, or by means of an explanted reservoir, wherein oral, intraperitoneal or intravenous administration route is preferred.

In the case of oral administration, the compound of the present invention may be made into any orally acceptable formulation form, including but not limited to tablets, capsules, aqueous solutions or aqueous suspensions. Wherein, the carrier used in tablets generally includes lactose and corn starch, additionally, a lubricant such as magnesium stearate may also be added. The diluent used in capsules generally includes lactose and dried corn starch. Aqueous suspensions are generally used by mixing active ingredient with suitable emulsifier and suspending agent. If desired, some sweetening agents, flavoring agents or coloring agents may also be added in the above oral formulation forms.

In the case of topical administration, especially for the treatment of affected surfaces or organs where topical application is easy to reach, such as eyes, skin, or lower intestinal neurological diseases, the compound of the present invention may be made into different topical formulation forms according to different affected surfaces or organs, which are specifically described as follows:

In the case of topical ocular administration, the compound of the present invention may be formulated into the formulation form of micronised suspension or solution, and the carrier used is isotonic sterile saline at a certain pH, to which a preservative such as benzyl chloride alkoxide may be added or not. For ocular administration, the compound may also be made into an ointment form such as Vaseline ointment.

In the case of topical dermal administration, the compound of the present invention may be made into suitable formulation forms of ointments, lotions or creams, wherein active ingredient is suspended or dissolved in one or more carriers. The carrier that may be used in ointments includes, but is not limited to: mineral oil, liquid petrolatum, white petrolatum, propylene glycol, polyoxyethylene, polyoxypropylene, emulsifying wax and water; the carrier that may be used in lotions or creams includes, but is not limited to: mineral oil, sorbitan monostearate, Tween 60, cetyl wax, hexadecene aromatic alcohols, 2-octyldodecanol, benzyl alcohol and water.

The compound of the present invention may also be administered in sterile injectable formulation forms, including sterile injectable aqueous or oil suspensions or sterile injectable solutions. The carrier and solvent that may be used therein include water, Ringer's solution and isotonic sodium chloride solution. In addition, sterile non-volatile oils, such as mono- or diglycerides, may also be used as solvent or suspending medium.

The dose of the compound of the present invention administered to the subject depends on the type and severity of the disease or condition and the characteristics of the subject, for example, general health condition, age, gender, body weight and tolerance to drugs, and also depends on the type of formulation and the administration route of drug, and the period or interval of administration, etc. Those skilled in the art can determine an appropriate dose according to these factors and other factors. Generally, the daily dose of the compound of the present invention useful for treating tumor may be about 1-800 mg, and this daily dose may be administered one or more times according to the specific condition. The compound of the present invention may be provided in dosage unit, and the content of the compound in the dosage unit may be 0.1-200 mg, e.g., 1-100 mg.

BENEFICIAL EFFECTS OF THE PRESENT INVENTION

The present invention provides a type of piperidine carboxamide compound having novel structure, which can effectively inhibit/reverse drug resistance of bacteria or tumors, and can act as Hsp70 inhibitor to effectively prevent an/or treat diseases or conditions caused by Hsp70. This provides a new medical strategy for the treatment of related diseases.

MODE OF CARRYING OUT THE INVENTION

The embodiments of the present invention will be described in detail in combination with the following examples. However, as will be appreciated by a person skilled in the art, the following examples are only used to illustrate the present invention, and should not be construed as limiting the scope of the present invention. The examples, in which the specific conditions are not indicated, are carried out according to conventional conditions or the conditions recommended by the manufacturer. The reagents or instruments, for which the manufacturers are not indicated, are all commercially available conventional products.

Melting point of the compound is measured using RY-1 melting point apparatus, with thermometer not corrected. Mass spectrum is measured using Micromass ZabSpec high resolution mass spectrometer (resolution 1000). $^1$H NMR is measured using JNM-ECA-400 superconducting NMR instrument, working frequency $^1$H NMR 300 MHz, $^{13}$C NMR 100 MHz.

Example 1 t-butyl N-methyl-N-[1-(4-chloropyrimidin-2-yl)piperidin-4-yl]carbamate

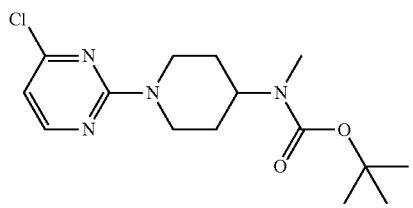 [SMILES: CN(C(=O)OC(C)(C)C)C1CCN(c2nccc(Cl)n2)CC1]

75 g of 2,4-dichloropyrimidine, 129 g of 4-N-t-butoxycarbonyl-4-N-methylaminopiperidine, 75 g of TEA and THF (700 ml, 10×) were added to a three-necked round-bottom flask, and reacted at room temperature. the reaction was completed after 2 h, and the reaction solution was evaporated under reduced pressure, followed by extracting with DCM and water twice, and washing with saturated saline solution twice. The organic phases were combined, dried with anhydrous sodium sulfate, and concentrated to obtain 190 g of a crude product. 500 mg of the crude product was separated through a chromatographic column, to give a product having less polarity, which was the target compound t-butyl N-methyl-N-[1-(4-chloropyrimidin-2-yl)piperidin-4-yl]carbamate of Example 1, and a product having more polarity, which was the target compound t-butyl N-methyl-N-[1-(2-chloropyrimidin-4-yl)piperidin-4-yl]carbamate of Example 2. $^1$H-NMR (300 MHz, CDCl$_3$-d) δ 1.49 (s, 9H); δ 1.62-1.69 (m, 2H); δ 1.74-1.73 (t, 2H); δ 2.73 (s, 3H); δ 2.89-2.95 (m, 2H); δ 4.28-4.32 (m, 2H); δ 4.86-4.90 (m, 2H); δ 6.49-6.51 (d, 1H); δ 8.15-8.16 (d, 1H). MS (TOF) 326.85 (M+).

Example 2 t-butyl N-methyl-N-[1-(2-chloropyrimidin-4-yl)piperidin-4-yl]carbamate

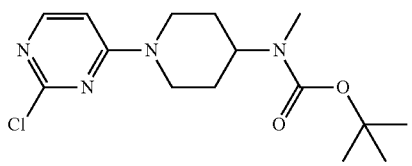

According to the method of Example 1, a product having more polarity was separated, which was the compound of Example 2. $^1$H-NMR (300 MHz, CDCl$_3$-d) δ 1.495 (s, 9H); δ 1.60-1.70 (m, 2H); δ 1.79-1.82 (t, 2H); δ 2.73 (s, 3H); δ 2.94-3.00 (t, 2H); δ 4.20-4.30 (m, 2H); δ 4.50-4.54 (m, 2H); δ 6.43-6.44 (d, 1H); δ 8.04-8.06 (d, 1H). MS (TOF) 326.85 (M+).

Example 3 t-butyl N-methyl-N-[1-(6-chloropyrimidin-4-yl)piperidin-4-yl]carbamate

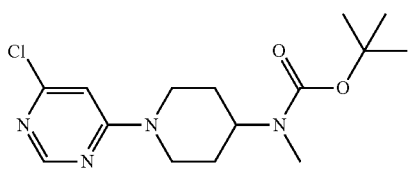 [SMILES: CN(C(=O)OC(C)(C)C)C1CCN(c2cc(Cl)ncn2)CC1]

The method of Example 1 was carried out, except for the use of 4,6-dichloropyrimidine in place of 2,4-dichloropyrimidine, to obtain 50 g of the product. $^1$H-NMR (300 MHz, CDCl$_3$-d) δ 1.47 (s, 9H); δ 1.60-1.61 (m, 2H); δ 1.63-1.64 (m, 2H); δ 2.79 (s, 3H); δ 2.91-2.97 (t, 2H); δ 4.25 (s, 1H); δ 4.48 (s, 2H); δ 6.52 (s, 1H); δ 8.36 (s, 1H). MS (TOF) 326.8 (M+).

Example 4 t-butyl N-methyl-N-[1-(4-methoxypyrimidin-2-yl)piperidin-4-yl]carbamate

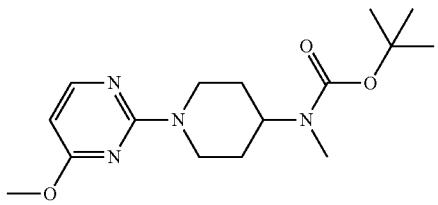 [SMILES: COc1ccnc(N2CCC(N(C)C(=O)OC(C)(C)C)CC2)n1]

190 g of the crude product obtained in Example 1 was dissolved in 800 ml of anhydrous methanol, to which 35 g (1.2 eq) of sodium methoxide was added slowly to carry out an exothermic reaction. T=70° C. and the reaction was completed after 6 h. The reaction solution was evaporated under reduced pressure, followed by extracting with DCM and water twice. The organic phases were combined, dried, concentrated and separated through a chromatographic column, to obtain 90 g of the target compound. $^1$H-NMR (300 MHz, CDCl$_3$-d) δ 1.46 (s, 9H); δ 1.60-1.72 (m, 4H); δ 2.70 (s, 3H); δ 2.82-2.90 (t, 2H); δ 3.88 (s, 3H); δ 4.84-4.89 (d, 1H); δ 5.95-5.96 (d, 1H); δ 8.02-8.04 (d, 1H). MS (TOF) 322.4 (M+).

Example 5 t-butyl N-methyl-N-[1-(2-methoxypyrimidin-4-yl)piperidin-4-yl]carbamate

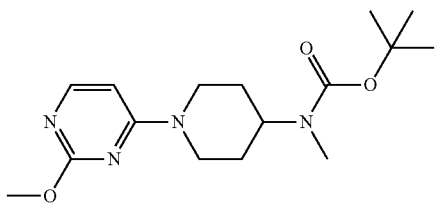 [SMILES: COc1nccc(N2CCC(N(C)C(=O)OC(C)(C)C)CC2)n1]

According to the method of Example 4, a product, which had less polarity than that of the product of Example 4, was separated through the chromatographic column, which was the target compound of Example 5, 40 g. $^1$H-NMR (300 MHz, CDCl$_3$-d) δ 1.46 (s, 9H); δ 1.62 (m, 2H); δ 1.72 (m, 2H); δ 2.70 (s, 3H); δ 2.90 (t, 2H); δ 3.91 (s, 3H); δ 4.49-4.51 (m, 3H); δ 6.18-6.19 (m, 2H); δ 8.00-8.01 (d, 1H). MS (TOF) 322.4 (M+).

Example 6 t-butyl N-methyl-N-[1-(2-methylthiopyrimidin-4-yl)piperidin-4-yl]carbamate

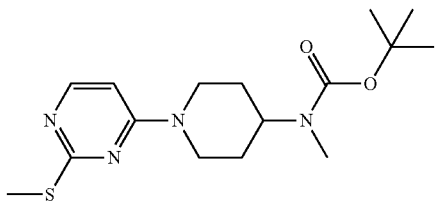

The method of Example 4 was carried out, with the use of the product obtained in Example 2 as starting material, and the use of sodium thiomethoxide in place of sodium methoxide, to obtain 36 g of the target compound. ¹H-NMR (300 MHz, CDCl₃-d) δ 1.494 (s, 9H); δ 1.615-1.651 (m, 2H); δ 1.752-1.785 (m, 2H); δ 2.521 (s, 3H) δ 2.724 (s, 3H); δ 2.892-2.953 (t, 2H); δ 4.200-4.529 (m, 2H); δ 4.532-4.569 (m, 2H); δ 6.223-6.239 (d, 1H); δ 8.025-8.040 (d, 1H). MS (TOF) 338.5 (M+).

Example 7 t-butyl N-methyl-N-[1-(6-methoxypyrimidin-4-yl)piperidin-4-yl]carbamate

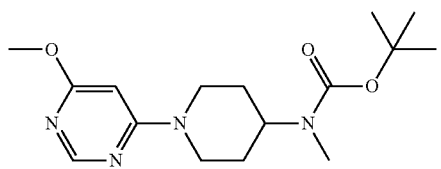 [SMILES: COc1cc(N2CCC(N(C)C(=O)OC(C)(C)C)CC2)ncn1]

The method of Example 4 was carried out, with the use of the compound as described in Example 3 as starting material, to obtain 33 g of the target compound. ¹H-NMR (300 MHz, CDCl₃-d) δ 1.47 (s, 9H); δ 1.55-1.65 (m, 2H); δ 1.72 (m, 2H); δ 2.70 (s, 3H); δ 2.89 (t, 2H); δ 3.91 (s, 3H); δ 4.20 (m, 1H); δ 4.42-4.45 (d, 2H); δ 5.84 (s, 1H); δ 8.32 (s, 1H). MS (TOF) 322.4 (M+).

Example 8

(1-t-butoxycarbonylpiperidin-4-yl) N-methyl-N-[1-(2-methylthiopyrimidin-4-yl)piperidin-4-yl]carbamate

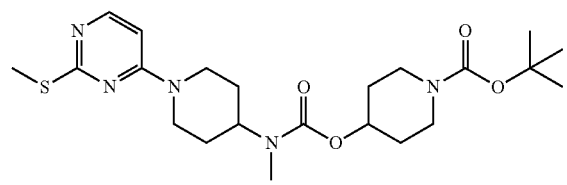 [SMILES: CSc1nccc(N2CCC(N(C)C(=O)OC3CCN(C(=O)OC(C)(C)C)CC3)CC2)n1]

The compound of Example 6 was added to concentrated hydrochloric acid for the removal of Boc, followed by the addition of potassium carbonate to obtain a free amine. 20 g (1 eq) of the resulting free amine was added to 200 ml of anhydrous DCM, to which 17 g (1.2 eq) of CDI was added with stirring. the reaction was completed after reacting at room temperature for 2 h, and the reaction solution was evaporated under reduced pressure, which was then dissolved in 200 ml DMF. 17 g of t-butyl 4-hydroxy-1-piperidinyl formate as starting material was dissolved in 200 ml DMF, to which 20 g NaH was added slowly; and the resulting solution was added dropwise to the above reaction solution after stirred for 30 min. the reaction was completed after 1 h, and the reaction solution was extracted with DCM and water twice. The organic phase was washed with saturated saline solution twice, dried, concentrated and separated through a chromatographic column, to obtain 10 g of a pure product. ¹H-NMR (300 MHz, CDCl₃-d) δ 1.4642 (s, 9H); δ 1.62-1.74 (m, 8H); δ 2.50 (s, 3H); δ 2.75 (s, 3H); δ 2.88-2.96 (t, 2H); δ 3.25-3.29 (m, 2H); δ 3.63-3.65 (m, 2H); δ 4.51-4.55 (m, 2H); δ 4.88-5.05 (m, 1H); δ 6.21-6.25 (d, 1H); δ 8.01-8.06 (d, 1H). MS (TOF) 465.6 (M+).

Example 9

(S)-(1-t-butoxycarbonylpyrrolidin-3-yl) N-methyl-N-[1-(2-methylthiopyrimidin-4-yl) piperidin-4-yl]carbamate

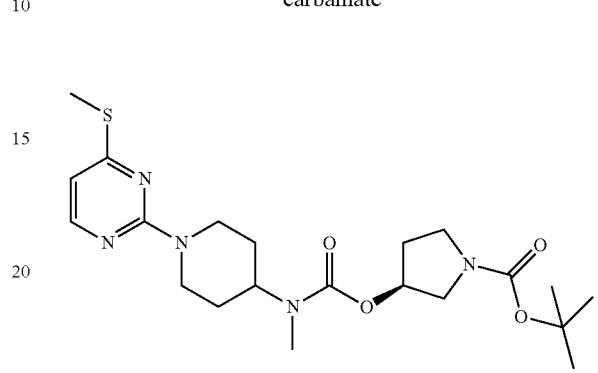

The method of Example 4 was carried out, with the use of sodium thiomethoxide in place of sodium methoxide, to obtain t-butyl N-methyl-N-[1-(4-methylthiopyrimidin-2-yl)piperidin-4-yl]carbamate. The method of Example 8 was carried out, with the use of the product obtained above as starting material, and the use of t-butyl (S)-3-hydroxypyrrolidin-1-yl formate in place of t-butyl 4-hydroxy-1-piperidinyl formate as starting material, to obtain 5 g of the product. ¹H-NMR (300 MHz, CDCl₃-d) δ 1.47 (s, 9H); δ 1.62-1.71 (m, 5H); δ 2.05 (m, 2H); δ 2.72 (s, 3H); δ 2.79-2.90 (m, 2H); δ 3.41-3.45 (m, 4H); δ 3.90 (s, 3H); δ 4.87-4.91 (m, 2H); δ 5.26-5.30 (m, 1H); δ 5.26-5.30 (m, 1H); δ 5.98-5.99 (d, 1H); δ 8.04-8.06 (d, 1H). MS (TOF) 435.5 (M+).

Example 10

(S)-(pyrrolidin-3-yl) N-methyl-N-[1-(2-methylthiopyrimidin-4-yl)piperidin-4-yl]carbamate hydrochloride

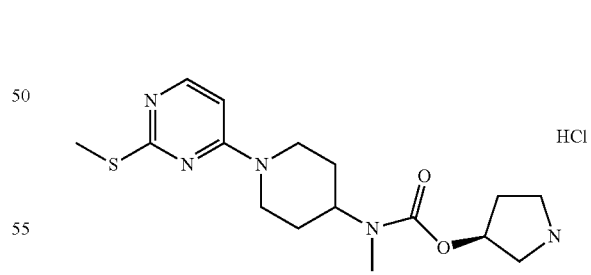

The product obtained in Example 6 was subject in sequence to the method of Example 8, and the removal of Boc, to obtain 6 g of the compound of Example 10, in which t-butyl (S)-3-hydroxypyrrolidin-1-yl formate was used in place of t-butyl (S)-4-hydroxy-1-piperidinyl formate as starting material. ¹H-NMR (300 MHz, CDCl₃-d) δ 1.099 (t, 1H); δ 1.685-1.787 (m, 4H); δ 2.208 (m, 2H); δ 2.686 (s, 3H); δ 2.977-3.042 (m, 1H); δ 3.400-3.422 (m, 1H); δ 3.459-3.562 (m, 5H); δ 4.118-4.153 (m, 2H); δ 4.712 (s, 3H); δ 5.124-5.156 (m, 1H); δ 5.288-5.294 (m, 1H); δ 6.645-6.664 (d, 1H); δ 7.761-7.780 (d, 1H). MS (TOF) 387.9 (M+).

Example 11

[1-(2,4-dichlorobenzenesulfonyl)piperidin-4-yl] N-methyl-N-[1-(2-methylthiopyrimidin-4-yl)piperidin-4-yl]carbamate

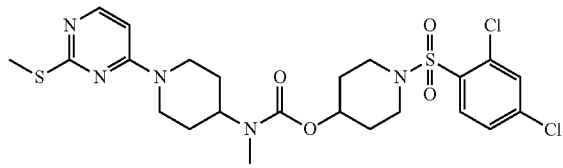 [SMILES: CSc1nccc(N2CCC(N(C)C(=O)OC3CCN(S(=O)(=O)c4ccc(Cl)cc4Cl)CC3)CC2)n1]

400 mg of the compound obtained in Example 8 was subject to the removal of BOC, followed by the addition of K₂CO₃ to obtain a free amine. The resulting free amine was dissolved in 3 ml THF, to carry out reaction at room temperature, with the addition of 0.5 g K₂CO₃, and 227 mg of 2,4-dichlorobenzenesulfonyl chloride. The reaction was completed after 4 h, and a small amount of water and ethyl acetate were added, followed by extracting with ethyl acetate three times, and washing with saturated sodium chloride solution twice. The organic phases were combined, dried with anhydrous sodium sulfate, concentrated and separated through a chromatographic column, to obtain 130 mg of the target compound. ¹H-NMR (300 MHz, CDCl₃-d) δ 1.64-1.81 (m, 6H); δ 1.96-2.05 (m, 2H); δ 2.50 (s, 3H); δ 2.72 (s, 3H); δ 2.91 (m, 2H); δ 3.26 (m, 2H); δ 3.51 (m, 2H); δ 4.30 (m, 1H); δ 4.51 (m, 2H); δ 4.86-4.87 (m, 1H); δ 6.20-6.22 (d, 1H); δ 7.26-7.36 (dd, 1H); δ 7.54-7.55 (d, 1H); δ 8.00 (s, 1H); δ 8.02-8.03 (t, 1H). MS (TOF) 574.5 (M+).

Example 12

(S)-[1-(imidazole-1-carbonyl)pyrrolidin-3-yl] N-methyl-N-[1-(2-methoxypyrimidin-4-yl) piperidin-4-yl]carbamate

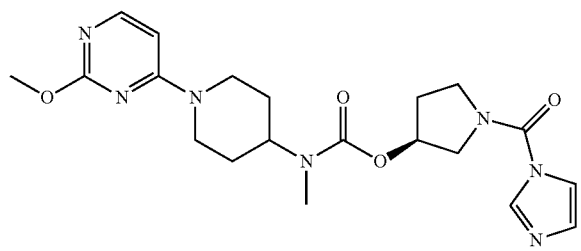 [SMILES: COc1nccc(N2CCC(N(C)C(=O)O[C@H]3CCN(C(=O)n4ccnc4)C3)CC2)n1]

The method of Example 10 was carried out, with the use of the product obtained in Example 5 as starting material. 20 g (1 eq) of the resulting BOC-removed product was added to 200 ml anhydrous DCM, to which 17 g (1.2 eq) of CDI was added with stirring, followed by reacting at room temperature for 2 h, and separating to obtain 20 g of the product. ¹H-NMR (300 MHz, CDCl₃-d) δ 1.24-1.28 (m, 4H); δ 1.65-1.74 (d, 1H); δ 2.05-2.23 (d, 1H); δ 2.73 (s, 3H); δ 2.94 (m, 2H); δ 3.70-3.78 (m, 4H); δ 3.93 (s, 3H); δ 4.3 (m, 1H); δ 4.53 (m, 2H); δ 5.30-5.35 (m, 1H); δ 6.20-6.35 (d, 1H); δ 7.11 (s, 3H); δ 7.36 (s, 3H); δ 8.03-8.05 (m, 2H). MS (TOF) 429.5 (M+).

Example 13

(S)-[1-(2-thienylsulfonyl)pyrrolidin-3-yl] N-methyl-N-[1-(2-methylthiopyrimidin-4-yl) piperidin-4-yl] carbamate The method of Example 11 was carried out, with the use of 2-thienylsulfonyl chloride in place of 2,4-dichlorobenzenesulfonyl chloride, to obtain 150 mg of the target compound. ¹H-NMR (300 MHz, CDCl₃-d) δ 1.54-1.68 (m, 4H); δ 2.04-2.07 (m, 2H); δ 2.42 (s, 2H); δ 2.50 (s, 2H); δ 2.75-2.90 (m, 3H); δ 3.36-3.54 (m, 4H); δ 4.24 (m, 1H); δ 4.50 (m, 1H); δ 5.15-5.30 (m, 1H); δ 6.20-6.23 (d, 1H); δ 7.14 (t, 1H); δ 7.60-7.61 (m, 2H); δ 8.01-8.03 (d, 1H). MS (TOF) 497.7 (M+).

Example 14 p-fluorophenylthio N-methyl-N-[1-(2-methoxypyrimidin-4-yl)piperidin-4-yl]carbamate

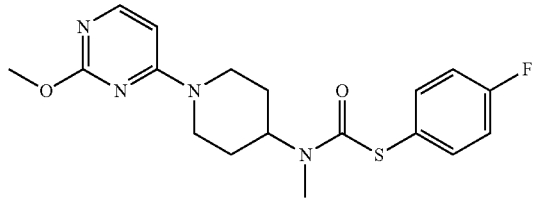

The product obtained in Example 5 was subject to the removal of Boc. 1 g of the resulting product was dissolved in 20 ml of anhydrous DCM, to which a suitable amount of 1 ml TEA was added with stirring. In ice-water bath, 1 g of triphosgene was dissolved in 5 ml of anhydrous DCM, and then the triphosgene solution was added dropwise slowly into the solution obtained above, with stirring continuously. After reacting for 1 h, 1 eq of p-aminothiophenol and 1 ml triethanolamine were added to continue the reaction at room temperature. The reaction was completed after 2 h, and 20 ml of water was added, followed by extracting with DCM three times, and washing with saturated sodium chloride solution twice. The organic phases were combined, dried with anhydrous sodium sulfate, concentrated and separated through a chromatographic column, to obtain 900 mg of the target compound. ¹H-NMR (300 MHz, CDCl₃-d) δ 1.73-1.85 (m, 5H); δ 2.77 (s, 5H); δ 3.96 (s, 3H); δ 4.57 (s, 3H); δ 6.23-6.24 (d, 1H); δ 7.09-7.13 (m, 2H); δ 7.47-7.51 (m, 2H); δ 8.05-8.07 (d, 1H). MS (TOF) 376.4 (M+).

Example 15 p-fluorophenylthio N-methyl-N-[1-(2-methylthiopyrimidin-4-yl)piperidin-4-yl]carbamate

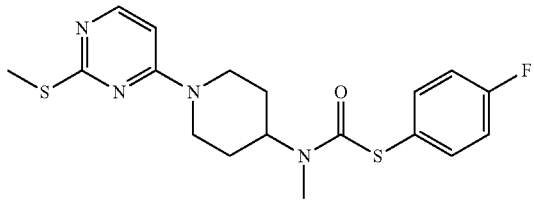 [SMILES: CSc1nccc(N2CCC(N(C)C(=O)Sc3ccc(F)cc3)CC2)n1]

The method of Example 14 was carried out, with the use of the product obtained in Example 6 as starting material, to obtain 550 mg of the target compound. $^{1}$H-NMR (300 MHz, CDCl$_3$-d) δ 1.72-1.84 (m, 5H); δ 2.53 (s, 3H); δ 2.94 (s, 5H); δ 2.67 (m, 3H); δ 6.24-6.25 (d, 1H); δ 7.09-7.13 (m, 2H); δ 7.47-7.51 (m, 2H); δ 8.05-8.06 (d, 1H). MS (TOF) 392.5 (M+).

Example 16

(1-acetylpiperidin-4-yl) N-methyl-N-[1-(4-methoxypyrimidin-2-yl)piperidin-4-yl]carbamate

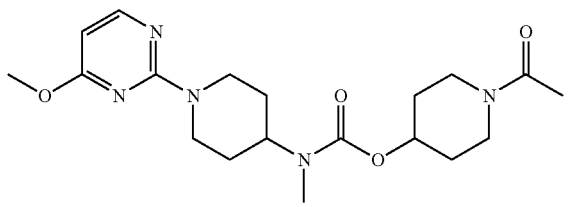 [SMILES: COc1ccnc(N2CCC(N(C)C(=O)OC3CCN(C(C)=O)CC3)CC2)n1]

The methods of Example 8 and Example 11 were respectively carried out, with the use of the product obtained in Example 4 as starting material, and the use of acetyl chloride in place of 2,4-dichlorobenzenesulfonyl chloride in Example 11, to obtain 160 mg of the target compound. $^{1}$H-NMR (300 MHz, CDCl$_3$-d) δ 1.66-1.71 (m, 6H); δ 1.92 (m, 2H); δ 2.11 (s, 3H); δ 2.77 (s, 3H); δ 2.89 (m, 2H); δ 3.37-3.84 (m, 4H); δ 3.88 (s, 3H); δ 4.30 (m, 1H); δ 4.88-4.91 (m, 3H); δ 5.97-5.98 (d, 1H); δ 8.04-8.05 (d, 1H). MS (TOF) 392.5 (M+).

Example 17

(S)-[1-(2-thienylsulfonyl)pyrrolidin-3-yl] N-methyl-N-[1-(4-methoxypyrimidin-2-yl) piperidin-4-yl]carbamate

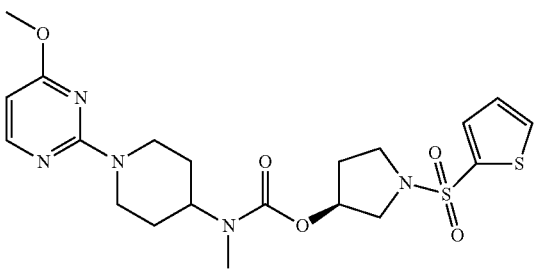 [SMILES: COc1ccnc(N2CCC(N(C)C(=O)O[C@H]3CCN(S(=O)(=O)c4cccs4)C3)CC2)n1]

The method of Example 11 was carried out, with the use of the product obtained in Example 9 as starting material, and the use of 2-thienylsulfonyl chloride in place of 2,4-dichlorobenzenesulfonyl chloride, to obtain 170 mg of the target compound. $^{1}$H-NMR (300 MHz, CDCl$_3$-d) δ 1.58-1.66 (m, 4H); δ 2.03-2.08 (m, 2H); δ 2.44 (s, 2H); δ 3.40-3.60 (m, 4H); δ 3.90 (s, 3H); δ 4.87-4.90 (d, 2H); δ 5.16 (s, 1H); δ 5.99-6.00 (d, 1H); δ 7.15 (m, 1H); δ 7.61-7.62 (t, 1H); δ 8.05-8.06 (d, 1H). MS (TOF) 481.6 (M+).

Example 18

[1-(3-chlorobenzyl)piperidin-3-yl] N-methyl-N[1-(2-methoxypyrimidin-4-yl)piperidin-4-yl] carbamate

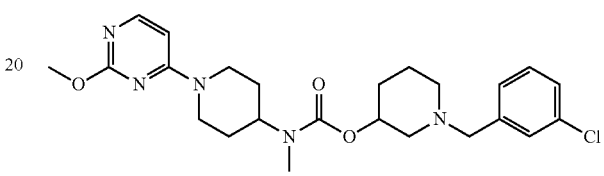

The methods of Example 8 and Example 11 were respectively carried out, with the use of the product obtained in Example 5 as starting material, the use of t-butyl 3-hydroxy-1-piperidinyl formate in place of t-butyl 4-hydroxy-2-piperidinyl formate in Example 8 as starting material, and the use of 3-chlorobenzyl chloride in place of 2,4-dichlorobenzenesulfonyl chloride in Example 11, to obtain 150 mg of the target compound. $^{1}$H-NMR (300 MHz, CDCl$_3$-d) δ 1.74-2.76 (m, 12H); δ 2.93 (s, 3H); δ 3.46 (m, 2H); δ 3.92 (s, 3H); δ 4.50-4.52 (m, 2H); δ 4.81 (s, 1H); δ 5.30 (s, 1H); δ 6.19-6.20 (d, 1H); δ 7.21-7.22 (m, 2H); δ 7.33 (s, 1H); δ 8.01-8.02 (d, 1H). MS (TOF) 474 (M+).

Example 19

[1-(3-chlorobenzyl)piperidin-4-yl] N-methyl-N-[1-(4-methoxypyrimidin-2-yl)piperidin-4-yl] carbamate

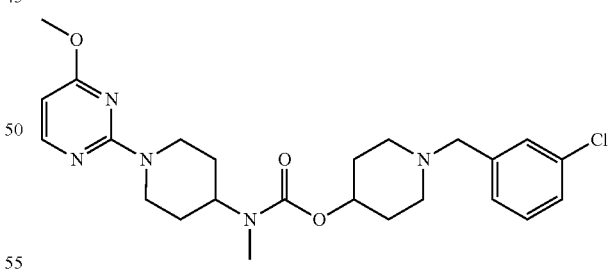

The methods of Example 8 and Example 11 were respectively carried out, with the use of the product obtained in Example 4 as starting material, and the use of 3-chlorobenzyl chloride in place of 2,4-dichlorobenzenesulfonyl chloride in Example 11, to obtain 145 mg of the target compound. $^{1}$H-NMR (300 MHz, CDCl$_3$-d) δ 1.65-1.80 (m, 6H); δ 1.95-1.98 (m, 2H); δ 2.36 (m, 2H); δ 2.65 (m, 2H); δ 2.66 (s, 2H); δ 2.77 (m, 2H); δ 3.51 (s, 2H); δ 3.90 (s, 2H); δ 4.79 (s, 1H); δ 4.89-4.92 (d, 2H); δ 5.98-5.99 (d, 1H); δ 7.23-7.28 (m, 3H); δ 7.36 (s, 1H); δ 8.05-8.07 (d, 1H). MS (TOF) 474 (M+).

Example 20

[1-(2,3-dichlorobenzenesulfonyl)piperidin-3-yl] N-methyl-N-[1-(2-methoxypyrimidin-4-yl) piperidin-4-yl]carbamate

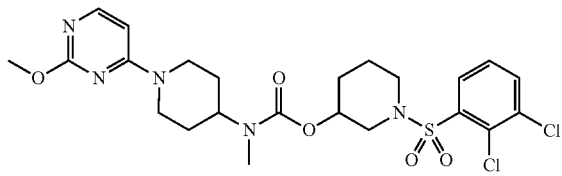 [SMILES: COc1nccc(N2CCC(N(C)C(=O)OC3CCCN(S(=O)(=O)c4cccc(Cl)c4Cl)C3)CC2)n1]

The methods of Example 8 and Example 11 were respectively carried out, with the use of the product obtained in Example 5 as starting material, the use of t-butyl 3-hydroxy-1-piperidinyl formate in place of t-butyl 4-hydroxy-1-piperidinyl formate in Example 8 as starting material, and the use of 2,3-dichlorobenzenesulfonyl chloride in place of 2,4-dichlorobenzenesulfonyl chloride in Example 11, to obtain 156 mg of the target compound. $^1$H-NMR (300 MHz, CDCl$_3$-d) δ 1.61-1.95 (m, 9H); δ 2.75-2.78 (m, 3H); δ 2.95 (m, 3H); δ 3.29 (m, 1H); δ 3.54 (d, 1H); δ 3.92 (m, 3H); δ 4.83 (m, 1H); δ 6.19-6.21 (d, 1H); δ 7.28-7.35 (m, 1H); δ 7.64-7.66 (d, 1H); δ 8.00-8.03 (d, 1H). MS (TOF) 558. 5 (M+).

Example 21

[1-(2,4-dichlorobenzenesulfonyl)piperidin-4-yl] N-methyl-N-[1-(2-methoxypyrimidin-4-yl) piperidin-4-yl]carbamate

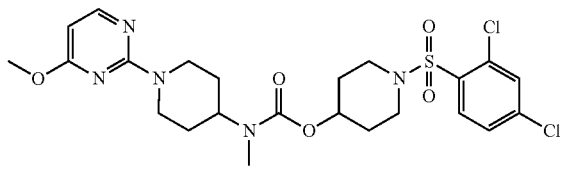 [SMILES: COc1ccnc(N2CCC(N(C)C(=O)OC3CCN(S(=O)(=O)c4ccc(Cl)cc4Cl)CC3)CC2)n1]

The methods of Example 8 and Example 11 were respectively carried out, with the use of the product obtained in Example 4 as starting material, to obtain 151 mg of the target compound. $^1$H-NMR (300 MHz, CDCl$_3$-d) δ 1.71-1.98 (m, 8H); δ 2.76 (s, 3H); δ 2.90 (s, 2H); δ 3.52 (m, 2H); δ 3.91 (s, 3H); δ δ 4.89-4.92 (d, 3H); δ 5.99-6.00 (d, 1H); δ 7.28-7.29 (d, 1H); δ 7.56 (s, 1H); δ 8.02-8.07 (m, 2H). MS (TOF) 558.5 (M+).

Example 22

[1-(4-fluorobenzyl)piperidin-3-yl] N-methyl-N-[1-(2-methoxypyrimidin-4-yl)piperidin-4-yl]carbamate

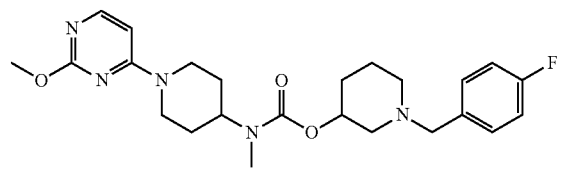 [SMILES: COc1nccc(N2CCC(N(C)C(=O)OC3CCCN(Cc4ccc(F)cc4)C3)CC2)n1]

The methods of Example 8 and Example 11 were respectively carried out, with the use of the product obtained in Example 5 as starting material, and the use of 4-fluorobenzyl chloride in place of 2,4-dichlorobenzenesulfonyl chloride in Example 11, to obtain 147 mg of the target compound. $^1$H-NMR (300 MHz, CDCl$_3$-d) δ 1.63-2.23 (m, 10H); δ 2.55 (m, 1H); δ 2.76 (s, 3H); δ 2.77 (m, 1H); δ 2.93 (t, 2H); δ 3.50 (m, 2H); δ 4.20-4.81 (m, 4H); δ 6.20-6.21 (d, 1H); δ 6.93-7.02 (t, 2H); δ 7.26-7.30 (m, 2H); δ 8.04-8.05 (d, 1H). MS (TOF) 457.5 (M+).

Example 23

(S)-[1-(2,3-dichlorobenzenesulfonyl)pyrrolidin-3-yl] N-methyl-N-[1-(2-methylthiopyrimidin-4-yl)piperidin-4-yl]carbamate

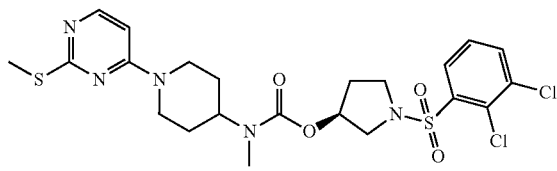 [SMILES: CSc1nccc(N2CCC(N(C)C(=O)O[C@H]3CCN(S(=O)(=O)c4cccc(Cl)c4Cl)C3)CC2)n1]

The method of Example 11 was carried out, with the use of the compound which has not been subject to the removal of Boc obtained in Example 10 as starting material, and the use of 2,3-dichlorobenzenesulfonyl chloride in place of 2,4-dichlorobenzenesulfonyl chloride, to obtain 165 mg of the target compound. $^1$H-NMR (300 MHz, CDCl$_3$-d) δ 1.50-1.80 (m, 4H); δ 2.18 (m, 2H); δ 2.52 (s, 3H); δ 2.65 (s, 3H); δ 2.93 (t, 2H); δ 3.60 (m, 4H); δ 4.20-4.30 (m, 1H); δ 4.54 (s, 2H); δ 5.31 (s, 1H); δ 6.22-6.23 (d, 1H); δ 7.28-7.36 (t, 1H); δ 8.03-8.07 (d, 1H). MS (TOF) 560.5 (M+).

Example 24

(S)-[1-(2,4-dichlorobenzenesulfonyl)pyrrolidin-3-yl] N-methyl-N-[1-(2-methylthiopyrimidin-4-yl)piperidin-4-yl]carbamate

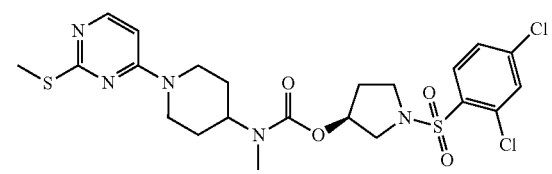 [SMILES: CSc1nccc(N2CCC(N(C)C(=O)O[C@H]3CCN(S(=O)(=O)c4ccc(Cl)cc4Cl)C3)CC2)n1]

The method of Example 11 was carried out, with the use of the compound which has not been subject to the removal of Boc obtained in Example 10 as starting material, to obtain 149 mg of the target compound. $^1$H-NMR (300 MHz, CDCl$_3$-d) δ 1.24-1.27 (m, 4H); δ 1.71-1.74 (m, 2H); δ 2.50 (s, 3H); δ 2.63 (s, 3H); δ 2.90 (t, 2H); δ 3.57-3.61 (m, 4H); δ 4.11-4.12 (m, 2H); δ 5.30 (m, 2H); δ 6.21-6.22 (d, 1H); δ 7.37-7.39 (d, 1H); δ 8.01-8.03 (m, 1H). MS (TOF) 560.5 (M+).

Example 25

(1-acetylpiperidin-3-yl) N-methyl-N-[1-(6-methoxy-pyrimidin-4-yl)piperidin-4-yl]carbamate

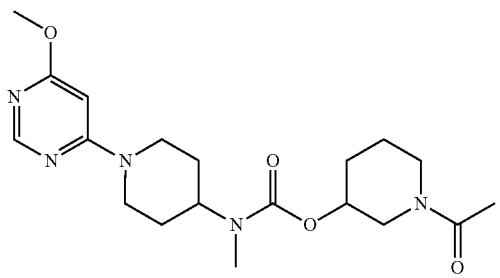 [SMILES: COc1cc(N2CCC(N(C)C(=O)OC3CCCN(C(C)=O)C3)CC2)ncn1]

The methods of Example 8 and Example 11 were respectively carried out, with the use of the product obtained in Example 7 as starting material, the use of t-butyl 3-hydroxy-1-piperidinyl formate in place of t-butyl 4-hydroxy-1-piperidinyl formate in Example 8 as starting material, and the use of acetyl chloride in place of 2,4-dichlorobenzenesulfonyl chloride in Example 11, to obtain 150 mg of the target compound. $^1$H-NMR (300 MHz, CDCl$_3$-d) δ 1.72-1.86 (m, 8H); δ 2.07-2.11 (m, 4H); δ 2.73 (s, 3H); δ 2.90-2.93 (m, 2H); δ 3.24 (t, 1H); δ 3.53-3.56 (m, 2H); δ 3.93 (s, 4H); δ 4.45-4.48 (d, 2H); δ 4.78 (m, 1H); δ 5.85 (s, 1H); δ 8. 33 (s, 1H). MS (TOF) 391.5 (M+).

Example 26

[1-(2,2,2-trifluoroacetyl)piperidin-3-yl] N-methyl-N-[1-(6-methoxypyrimidin-4-yl) piperidin-4-yl]carbamate

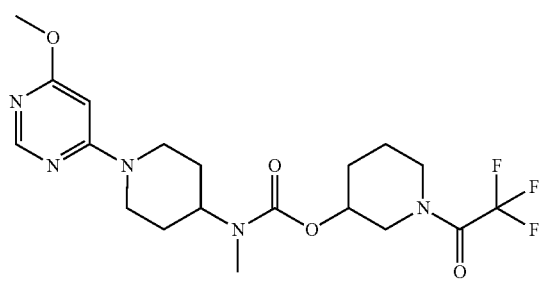 [SMILES: COc1cc(N2CCC(N(C)C(=O)OC3CCCN(C(=O)C(F)(F)F)C3)CC2)ncn1]

The methods of Example 8 and Example 11 were respectively carried out, with the use of the product obtained in Example 7 as starting material, the use of t-butyl 3-hydroxy-1-piperidinyl formate in place of t-butyl 4-hydroxy-1-piperidinyl formate in Example 8 as starting material, and the use of 3,3,3-trifluoroacetyl chloride in place of 2,4-dichlorobenzenesulfonyl chloride in Example 11, to obtain 156 mg of the target compound. $^1$H-NMR (300 MHz, CDCl$_3$-d) δ 1.72-1.88 (m, 8H); δ 2.78 (s, 3H); δ 2.78-3.14 (m, 4H); δ 3.93 (s, 5H); δ 4.20-4.47 (m, 3H); δ 4.93 (m, 1H); δ 5.83 (s, 1H); δ 8.33 (s, 1H). MS (TOF) 445.4 (M+).

Example 27

[1-(imidazole-1-carbonyl)piperidin-3-yl] N-methyl-N[1-(6-methoxypyrimidin-4-yl) piperidin-4-yl]carbamate

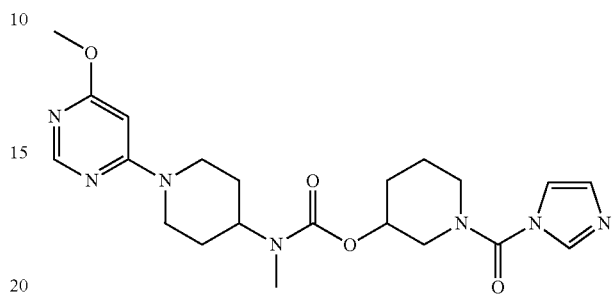

The methods of Example 8 and Example 11 were respectively carried out, with the use of the product obtained in Example 7 as starting material, the use of t-butyl 3-hydroxy-1-piperidinyl formate in place of t-butyl 4-hydroxy-1-piperidinyl formate in Example 8 as starting material, and the use of CDI in place of 2,4-dichlorobenzenesulfonyl chloride in Example 11, to obtain 153 mg of the target compound. $^1$H-NMR (300 MHz, CDCl$_3$-d) δ 1.73 (m, 5H); 1.95-2.10 (m, 3H); δ 2.75 (s, 3H); δ 2.90 (m, 2H); δ 3.37-3.39 (s, 1H); δ 3.62 (d, 1H); δ 3.84-3.85 (d, 2H); δ 3.92 (s, 3H); δ 4.26 (m, 1H); δ 4.74 (m, 2H); δ 4.91 (s, 1H); δ 5.87 (s, 1H); δ 7.11 (s, 1H); δ 7.22 (s, 1H); δ 7.89 (s, 1H); δ 8.34 (s, 1H). MS (TOF) 443.5 (M+).

Example 28

[1-(2-thienylsulfonyl)piperidin-3-yl] N-methyl-N-[1-(2-methoxypyrimidin-4-yl)piperidin-4-yl]carbamate

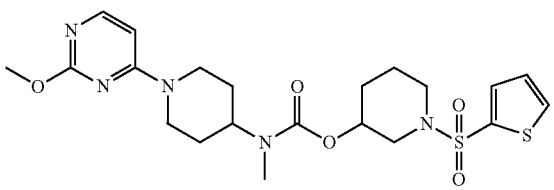 [SMILES: COc1nccc(N2CCC(N(C)C(=O)OC3CCCN(S(=O)(=O)c4cccs4)C3)CC2)n1]

The methods of Example 8 and Example 11 were respectively carried out, with the use of the product obtained in Example 5 as starting material, and the use of 2-thienylsulfonyl chloride in place of 2,4-dichlorobenzenesulfonyl chloride in Example 11, to obtain 155 mg of the target compound. $^1$H-NMR (300 MHz, CDCl$_3$-d) δ 1.26 (m, 2H); δ 1.68-1.91 (m, 9H); δ 2.78 (s, 4H); δ 2.96-3.17 (m, 3H); δ 3.94 (s, 3H); δ 4.12-4.53 (m, 3H); δ 6.21-6.22 (d, 1H); δ 7.13-7.14 (m, 1H); δ 7.53-7.54 (m, 1H); δ 7.60-7.61 (d, 1H); δ 8.03-8.04 (m, 1H). MS (TOF) 495.6 (M+).

Example 29

1-(1-thienylsulfonyl)piperidin-4-yl] N-methyl-N-[1-(4-methoxypyrimidin-2-yl)piperidin-4-yl]carbamate

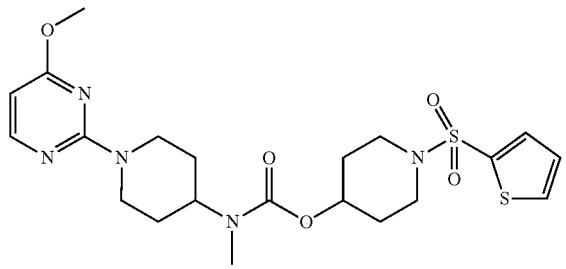 [SMILES: COc1ccnc(N2CCC(N(C)C(=O)OC3CCN(S(=O)(=O)c4cccs4)CC3)CC2)n1]

The methods of Example 8 and Example 11 were respectively carried out, with the use of the product obtained in Example 4 as starting material, and the use of 2-thienylsulfonyl chloride in place of 2,4-dichlorobenzenesulfonyl chloride in Example 11, to obtain 150 mg of the target compound. $^1$H-NMR (300 MHz, CDCl$_3$-d) δ 1.73 (m, 2H); 1.95-2.10 (m, 2H); δ 2.19 (s, 5H); δ 2.65 (m, 3H); δ 2.70-3.39 (m, 7H); δ 3.90 (s, 3H); δ 4.84 (m, 3H); δ 4.74 (m, 2H); δ 5.97 (dd, 1H); δ 7.17 (m, 1H); δ 7.57 (t, 1H); δ 7.63 (t, 1H); δ 8.10 (dd, 1H). MS (TOF) 495.6 (M+).

Example 30

N-methyl-N-[1-(4-chloropyrimidin-2-yl)piperidin-4-yl]-[2-(imidazol-1-yl)]acetamide

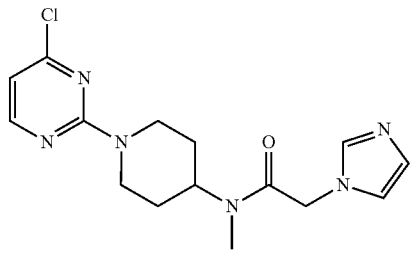 [SMILES: CN(C(=O)Cn1ccnc1)C1CCN(c2nccc(Cl)n2)CC1]

10 g (1 eq) of the compound obtained in Example 1 was added to a 250 ml three-necked round-bottom flask, to which trifluoroacetic acid was added for the removal of Boc, followed by the addition of potassium carbonate to obtain a free amine. The resulting free amine was dissolved in dichloromethane, to which 6.8 g (1.5 eq) of triethylamine was added, and then 6 g (1.2 eq) of chloroacetyl chloride was added dropwise slowly within 30 min in ice-water bath. The reaction was completed after 1 h, and the reaction solution was extracted with dichloromethane and water twice. The organic phases were combined, dried and concentrated to obtain a crude product. 400 mg of the crude product was subject to further reaction by adding in sequence 5 ml DMF, 500 mg K$_2$CO$_3$, and 200 mg imidazole. The reaction was completed after 4 h, and the reaction solution was added dropwise slowly to water, to precipitate out 100 mg of the target compound. $^1$H-NMR (300 MHz, CDCl$_3$-d) δ 1.63-1.71 (m, 2H); 1.74-1.77 (m, 2H); δ 2.87-2.99 (m, 5H); δ 4.75 (m, 1H); δ 4.85-4.99 (m, 4H); δ 6.25-6.53 (dd, 1H); δ 7.02 (s, 1H); δ 7.15 (s, 1H); δ 7.71 (s, 1H); δ 8.16-8.17 (dd, 1H). MS (TOF) 334.8 (M+).

Example 31

N-methyl-N-[1-(4-chloropyrimidin-2-yl)piperidin-4-yl]-2-(1H-1,2,4-triazol-1-yl)acetamide

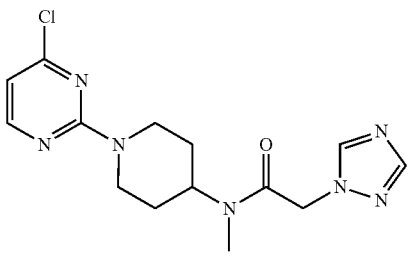 [SMILES: CN(C(=O)Cn1cncn1)C1CCN(c2nccc(Cl)n2)CC1]

The method of Example 30 was carried out, with the use of 1H-1,2,4-triazole in place of imidazole, to obtain 110 mg of the target compound. $^1$H-NMR (300 MHz, CDCl$_3$-d) δ 1.63-1.76 (m, 4H); δ 2.85-2.97 (m, 5H); δ 4.72 (m, 1H); δ 4.88-4.92 (m, 4H); δ 5.06 (s, 2H); δ 6.51-6.52 (dd, 1H); δ 7.98 (s, 1H); δ 8.15-8.16 (dd, 1H); δ 8.26 (s, 1H). MS (TOF) 335.8 (M+).

Example 32

N-methyl-N-[1-(2-chloropyrimidin-4-yl)piperidin-4-yl]-2-(2-chlorobenzoimidazol-1-yl) acetamide

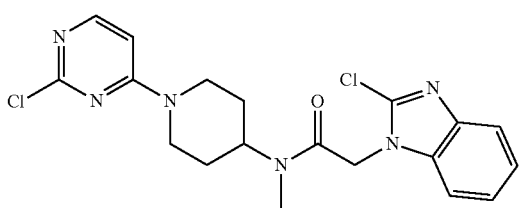 [SMILES: CN(C(=O)Cn1c(Cl)nc2ccccc21)C1CCN(c2ccnc(Cl)n2)CC1]

The method of Example 30 was carried out, with the use of the compound obtained in Example 2 as starting material, and the use of 2-chloro-benzoimidazole in place of imidazole, to obtain 111 mg of the target compound. $^1$H-NMR (300 MHz, CDCl$_3$-d) δ 1.66-1.70 (m, 2H); δ 1.79-1.82 (m, 2H); δ 2.86-3.00 (m, 5H); δ 4.54 (s, 2H); δ 4.73 (m, 1H); δ 4.97 (s, 2H); δ 6.42-6.44 (d, 1H); δ 7.21-7.22 (m, 1H); δ 7.28-7.31 (dd, 1H); δ 7.72-7.40 (dd, 1H), δ 8.05-8.06 (d, 1H). MS (TOF) 419.3 (M+).

Example 33

N-methyl-N-[1-(6-methoxypyrimidin-4-yl)piperidin-4-yl]-[2-(imidazol-1-yl)]acetamide

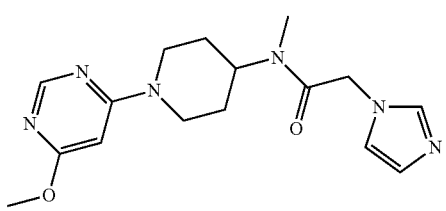 [SMILES: COc1cc(N2CCC(N(C)C(=O)Cn3ccnc3)CC2)ncn1]

10 g (1 eq) of the compound obtained in Example 7 was added to a 250 ml three-necked round-bottom flask, to which 6.8 g (1.5 eq) of triethylamine was added, and then 6 g (1.2 eq) of chloroacetyl chloride was added dropwise slowly within 30 min in ice-water bath. The reaction was completed after 1 h, and the reaction solution was extracted with dichloromethane and water twice; the organic phases were combined, dried and concentrated to obtain a crude product; 400 mg of the crude product was subject to further reaction by adding in sequence 5 ml DMF, 500 mg $K_2CO_3$, and 200 mg imidazole. The reaction was completed after 4 h, and the reaction solution was added dropwise slowly to water, to precipitate out 100 mg of the target compound. $^1$H-NMR (300 MHz, $CDCl_3$-d) δ 1.63-1.75 (m, 4H); δ 2.85-2.97 (m, 5H); δ 3.92 (s, 3H); δ 4.45-4.49 (m, 2H); δ 4.79 (s, 2H); δ 6.98 (s, 1H); δ 7.12 (s, 1H); δ 7.54 (s, 1H); δ 8.33 (s, 1H). MS (TOF) 330.4 (M+).

Example 34

N-methyl-N-[1-(6-methoxypyrimidin-4-yl)piperidin-4-yl]-2-(1H-1,2,4-triazol-1-yl) acetamide

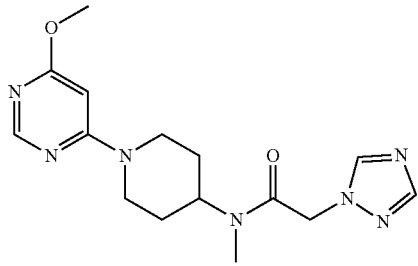 [SMILES: COc1cc(N2CCC(N(C)C(=O)Cn3cncn3)CC2)ncn1]

The method of Example 33 was carried out, with the use of 1H-1,2,4-triazole in place of imidazole, to obtain 113 mg of the target compound. $^1$H-NMR (300 MHz, $CDCl_3$-d) δ 1.63-1.74 (m, 4H); δ 2.84-2.95 (m, 5H); δ 3.91 (s, 3H); δ 4.44-4.48 (m, 2H); δ 4.72 (m, 2H); 5.05 (s, 2H); δ 5.84 (s, 1H); δ 7.97 (s, 1H); δ 8.25 (s, 1H); δ 8.32 (s, 1H). MS (TOF) 331.4 (M+).

Example 35

N-methyl-N-[1-(6-methoxypyrimidin-4-yl)piperidin-4-yl]-2-(2-chlorobenzoimidazol-1-yl) acetamide

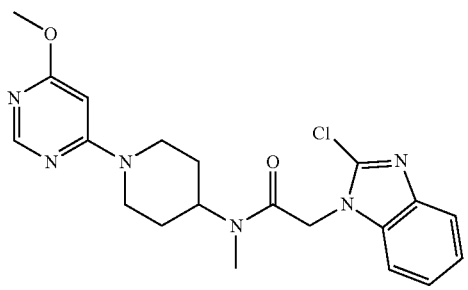 [SMILES: COc1cc(N2CCC(N(C)C(=O)Cn3c(Cl)nc4ccccc43)CC2)ncn1]

The method of Example 33 was carried out, with the use of 2-chloro-benzoimidazole in place of imidazole, to obtain 101 mg of the target compound. $^1$H-NMR (300 MHz, $CDCl_3$-d) δ 1.68-1.72 (m, 4H); δ 2.85-2.93 (dd, 4H); δ 2, 97 (s, 3H); δ 3.93 (s, 3H); δ 4.45-4.48 (m, 2H); δ 4.72 (m, 1H); δ 4.94 (s, 2H); δ 5.85 (s, 1H); δ 7.20-7.21 (dd, 1H); δ 7.28-7.30 (d, 1H); δ 7.71-7.73 (dd, 1H), δ 8.34 (s, 1H). MS (TOF) 414.9 (M+).

Example 36

N-methyl-N-[1-(2-methylthiopyrimidin-4-yl)piperidin-4-yl]-2-{[3-(1,2,4-triazol-1-methyl)] pyrrolidin-1-yl}acetamide

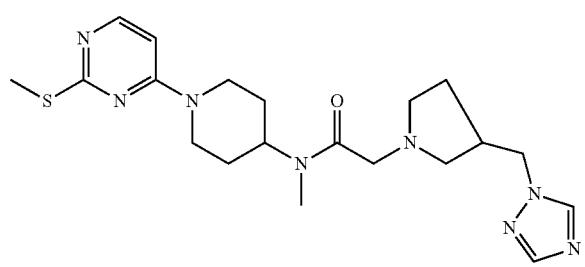 [SMILES: CSc1nccc(N2CCC(N(C)C(=O)CN3CCC(Cn4cncn4)C3)CC2)n1]

The method of Example 33 was carried out, with the use of the compound obtained in Example 6 as starting material, and the use of pyrrolidine-3-methyl-1H-1,2,4-triazole in place of imidazole, to obtain 150 mg of the target compound. $^1$H-NMR (300 MHz, $CDCl_3$-d) δ 1.43-1.68 (m, 7H); δ 2.00-2.10 (m, 1H); δ 2, 51 (s, 3H); δ 2.74 (m, 1H); δ 2.77 (s, 3H); δ 2.85-2.97 (m, 2H); δ 3.17-3.60 (m, 3H); δ 3.32 (m, 2H); δ 4.14-4.15 (m, 2H); δ 4.54 (s, 2H); δ 4.74 (m, 1H); δ 6.21-6.22 (d, 1H); δ 7.93 (s, 1H); δ 8.02-8.04 (d, 1H), δ 8.20 (s, 1H). MS (TOF) 430.6 (M+).

Example 37

N-methyl-N-[1-(2-methoxypyrimidin-4-yl)piperidin-4-yl]-2-{[2-(1H-1,2,4-triazol-1-methyl)]pyrrolidin-1-yl}acetamide

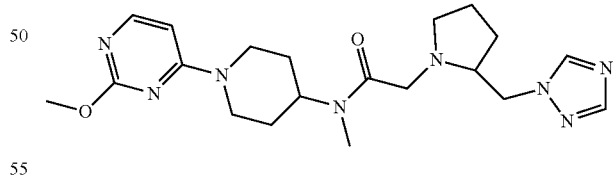

The method of Example 33 was carried out, with the use of the compound obtained in Example 5 as starting material, and the use of pyrrolidine-3-methyl-1H-1,2,4-triazole in place of imidazole, to obtain 110 mg of the target compound. $^1$H-NMR (300 MHz, $CDCl_3$-d) δ 1.62-1.66 (m, 7H); δ 1.69-1.72 (m, 1H); δ 2, 73 (s, 3H); δ 2.78 (m, 1H); δ 2.97 (m, 2H); δ 3.17-3.20 (d, 2H); δ 3.34-3.38 (d, 2H); δ 3.94 (s, 3H); δ 4.15-4.15 (m, 2H); δ 4.54 (s, 2H); δ 4.74 (m, 1H); δ 6.20-6.22 (d, 1H); δ 7.93 (s, 1H); δ 8.04-8.05 (d, 1H), δ 8.21 (s, 1H). MS (TOF) 414.5 (M+).

Example 38

N-methyl-N-[1-(6-methoxypyrimidin-4-yl)piperidin-4-yl]-2-{[2-(1H-1,2,4-triazol-1-methyl)]pyrrolidin-1-yl}acetamide

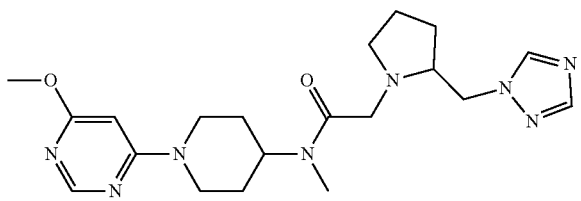 [SMILES: COc1cc(N2CCC(N(C)C(=O)CN3CCCC3Cn3cncn3)CC2)ncn1]

The method of Example 33 was carried out, with the use of the compound obtained in Example 7 as starting material, and the use of pyrrolidine-3-methyl-1H-1,2,4-triazole in place of imidazole, to obtain 110 mg of the target compound. $^1$H-NMR (300 MHz, CDCl$_3$-d) δ 1.61-1.67 (m, 7H); δ 1.67-1.70 (m, 1H); δ 2, 73 (s, 3H); δ 2.77 (m, 1H); δ 2.94 (m, 2H); δ 3.16-3.20 (d, 2H); δ 3.29 (d, 2H); δ 3.92 (s, 3H); δ 4.13-4.15 (m, 2H); δ 4.43-4.47 (d, 2H); δ 4.72 (m, 1H); δ 5.84 (s, 1H); δ 7.92 (s, 1H); δ 8.20 (s, 1H), δ 8.32 (s, 1H). MS (TOF) 414.5 (M+).

Example 39

N-methyl-N-[1-(4-methoxypyrimidin-2-yl)piperidin-4-yl]-2-{[2-(1H-1,2,4-triazol-1-methyl)]pyrrolidin-1-yl}acetamide

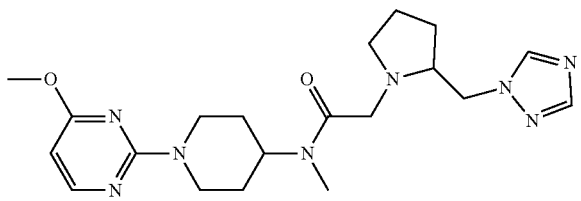 [SMILES: COc1ccnc(N2CCC(N(C)C(=O)CN3CCCC3Cn3cncn3)CC2)n1]

The method of Example 33 was carried out, with the use of the compound obtained in Example 4 as starting material, and the use of pyrrolidine-3-methyl-1H-1,2,4-triazole in place of imidazole, to obtain 109 mg of the target compound. $^1$H-NMR (300 MHz, CDCl$_3$-d) δ 1.59-1.65 (m, 6H); δ 1.66-1.69 (m, 1H); δ 2.04 (m, 1H); δ 2, 76 (m, 1H); δ 2, 79 (s, 3H); δ 2.93 (m, 2H); δ 3.19-3.22 (m, 2H); δ 3.35-3.39 (d, 2H); δ 3.90 (s, 3H); δ 4.16 (m, 2H); δ 4.88-4.92 (m, 1H); δ 5.31 (m, 1H); δ 5.99-6.00 (d, 1H); δ 7.93 (s, 1H); δ 8.04-8.06 (d, 1H), δ 8.21 (s, 1H). MS (TOF) 414.5 (M+).

Example 40

N-methyl-N-[1-(6-methoxypyrimidin-4-yl)piperidin-4-yl]-2-(1H-1,2,4-triazol-1-yl) acetamide

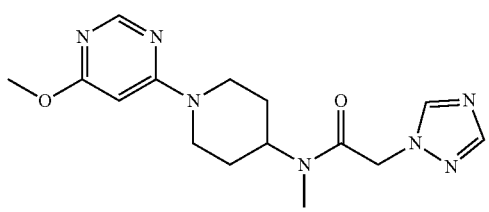 [SMILES: COc1cc(N2CCC(N(C)C(=O)Cn3cncn3)CC2)ncn1]

The method of Example 33 was carried out, with the use of the compound obtained in Example 7 as starting material, and the use of 1,2,4-triazole in place of imidazole, to obtain 115 mg of the target compound. $^1$H-NMR (300 MHz, CDCl$_3$-d) δ 1.37-1.40 (m, 3H); δ 1.98-2.02 (m, 2H); δ 3.06-3, 07 (m, 2H); δ 3.93 (s, 3H); δ 4.07-4.09 (m, 1H); δ 4.23-4.26 (m, 2H); δ 4.87 (s, 2H); δ 5.84 (s, 1H); δ 6.40 (s, 1H); δ 8.06 (s, 1H); δ 8.20 (s, 1H); δ 8.34 (s, 1H). MS (TOF) 400.9 (M+).

Example 41

N-methyl-N-[1-(6-methylpyrimidin-4-yl)piperidin-4-yl]-2-(2-chloro-benzoimidazol-1-yl) acetamide

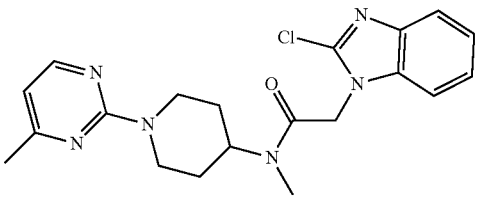 [SMILES: Cc1ccnc(N2CCC(N(C)C(=O)Cn3c(Cl)nc4ccccc43)CC2)n1]

The methods of Example 1 and Example 33 were respectively carried out, with the use of 2-chloro-4-methylpyrimidine as starting material, and the use of 2-chloro-benzoimidazole in place of imidazole in Example 33, to obtain 105 mg of the target compound. $^1$H-NMR (300 MHz, CDCl$_3$-d) δ 1.70-1.73 (m, 4H); δ 2.35 (s, 3H); δ 2.86-2.93 (m, 3H); δ 2.98 (s, 2H); δ 4.95 (m, 1H); δ 4.98 (s, 3H); δ 5.06 (m, 1H); δ 6.39-6.40 (d, 1H); δ 7.23-7.21 (dd, 1H); δ 7.29-7.30 (m, 2H); δ 7.71-7.74 (t, 1H), δ 8.17-8, 20 (d, 1H). MS (TOF) 398.9 (M+).

Example 42

N-methyl-N-[1-(4-methoxypyrimidin-2-yl)piperidin-4-yl]-2-(1H-1,2,4-triazol-1-yl) acetamide

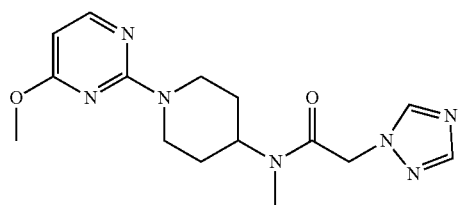 [SMILES: COc1ccnc(N2CCC(N(C)C(=O)Cn3cncn3)CC2)n1]

The method of Example 33 was carried out, with the use of the compound obtained in Example 4 as starting material, and the use of 1,2,4-triazole in place of imidazole, to obtain 120 mg of the target compound. $^1$H-NMR (300 MHz, CDCl$_3$-d) δ 1.65-1.73 (m, 4H); δ 2.84-2.89 (m, 2H); δ 2.92 (s, 3H); δ 3.88 (s, 3H); δ 4.60-4.71 (m, 1H); δ 4.87-4.90 (m, 2H); δ 5.05 (s, 2H); δ 5.96-5.89 (d, 1H); δ 7.91 (s, 1H); δ 8.02-8.04 (d, 1H), δ 8.26 (s, 1H). MS (TOF) 331.4 (M+).

Example 43

N-methyl-N-[1-(2-methoxypyrimidin-4-yl)piperidin-4-yl]-2-(1H-1,2,4-triazol-1-yl) acetamide

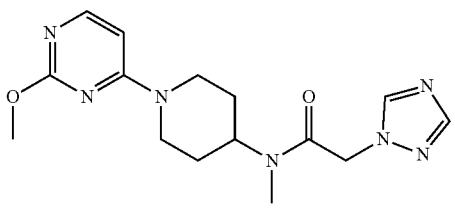 [SMILES: COc1nccc(N2CCC(N(C)C(=O)Cn3cncn3)CC2)n1]

The method of Example 33 was carried out, with the use of the compound obtained in Example 5 as starting material, and the use of 1,2,4-triazole in place of imidazole, to obtain 150 mg of the target compound. $^1$H-NMR (300 MHz, CDCl$_3$-d) δ 1.63-1.77 (m, 4H); δ 2.94 (s, 3H); δ 2.96-2.99 (m, 2H); δ 3.94-3.95 (s, 3H); δ 4.56 (m, 1H); δ 4.74 (m, 2H); δ 5.07 (s, 2H); δ 6.21-6.22 (d, 1H); δ 7.98 (s, 1H); δ 8.04-8.06 (d, 1H), δ 8.26 (s, 1H). MS (TOF) 331.4 (M+).

Example 44

N-methyl-N-[1-(2-methylthiopyrimidin-4-yl)piperidin-4-yl]-2-(1H-1,2,4-triazol-1-yl) acetamide

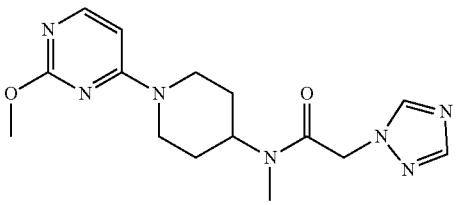 [SMILES: COc1nccc(N2CCC(N(C)C(=O)Cn3cncn3)CC2)n1]

The method of Example 33 was carried out, with the use of the compound obtained in Example 6 as starting material, and the use of 1,2,4-triazole in place of imidazole, to obtain 125 mg of the target compound. $^1$H-NMR (300 MHz, CDCl$_3$-d) δ 1.63-1.77 (m, 4H); δ 2.50 (s, 3H); δ 2.83-2.93 (m, 5H); δ 4.53-4.56 (m, 2H); δ 4.72 (m, 1H); δ 5.06 (s, 2H); δ 6.21-6.22 (d, 1H); δ 7.98 (s, 1H); δ 8.02-8.03 (d, 1H), δ 8.24 (s, 1H). MS (TOF) 347.4 (M+).

Example 45 Antitumor Bioactivity Evaluation of Compounds of the Present Invention 1. Test Materials Cells:

| Name | Generation | Survival rate % |
|---|---|---|
| BT474 | P103 | 100 |
| BT/Lap$^R$1.0 | / | 97.12 |
| MDA-MB-361 | F72 | 97.76 |
| SK-BR3 | F28 | 95.95 |
| SK/Lap$^R$1.0 | / | 93.35 |
| MDA-MB-453 | F8 | 96.8 |

Note:
BT474, SK-BR3 are human breast cancer cell lines sensitive to lapatinib, BT/LapR, SK/LapR are human breast cancer cell lines with secondary resistance to lapatinib after being stimulated with lapatinib, MDA-MB-361 and MDA-MB-453 are human breast cancer cell lines with natural resistance to lapatinib. BT474, MDA-MB-361, SK-BR3 and MDA-MB-453 all come from American Type Culture Collection (ATCC).

Lapatinib: 10 Mm in DMSO, BioVision, Cat: 1624-100, Lot: 50324;

ATPlit kit: CellTiter-Glo Substrate, Promega, Part: G755B, Lot: 32513501, EXP: 2014-05.

2. Experimental Procedures

Cells plating: a 100 mm culture dish with overgrown adherent cells was digested with 1 ml 0.25% trypsin (GIBCO) at 37° C. for 5 min, and the reaction was terminated with 2 ml culture medium (containing 10% FBS, GIBCO). The cells were scattered and collected, after counting, diluted to 1×10$^5$ cells/ml, and seeded into a 96-well plate at 50 μl/well, 5000 cells/well, excluding the peripheral circle of wells to which no cell was added, but PBS was added, 60 wells in total, and then incubated at 37° C. for 24 hours for adhering.

Addition of compound and lapatinib: the test sample was diluted to a final concentration of 5 μM, culture medium with the corresponding compound solvent concentration was filled in control well, the compound solvent concentration was kept consistent in each well, 5 parallel wells were set for each concentration, 25 μl each well, 25 μl culture medium (in combined group, 25 μl lapatinib was added till a final concentration of 1 μM) supplemented, followed by incubation at 37° C. for 72 hours.

Test after incubation at 37° C. for 72 hours: 50 of ATPlite kit substrate solution was added in each well, and vibrated for 3 min, followed by placing aside in darkness for 10 min, and then supernatant 100 μl/well was taken and placed on aluminescence test plate; the luminescence test plate that has been fully incubated was placed in a luminescence test instrument, to read luminescence value.

3. Data Processing (1) Cell survival rate (%)=Experimental group RLU/ control group RLU×100%. The experimental data were subjected to data analysis and processing by utilizing Graph-Pad software. The results were shown in Table 1.

(2) The nature of interaction between two drugs was evaluated by using coefficient of drug interaction (CDI), CDI being calculated as follows: CDI=AB/(A×B)×100%. As calculated according to the number of viable cells (luminescence value), when CDI<1, the nature of interaction between two drugs is synergism; when CDI<0.7, the synergism is very significant; when CDI=1, the nature of interaction between two drugs is addition; when CDI>1, the nature of interaction between two drugs is antagonism.

The coefficient of drug interaction (CDI) between the compound of Example 30 and Lapatinib was shown in Table 1: CDI was less than 1 in both breast cancer MDA-MB-361 and SK/Lap$^R$1.0 cell lines, in particular CDI<0.7 in SK/Lap$^R$1.0, which indicated that the synegerism between the compound of Example 30 and Lapatinib was very significant.

TABLE 1

| Cell | Example 30 (μM) | RLU | | | | | Average | Survival rate % |
|---|---|---|---|---|---|---|---|---|
| BT474 | 10 | 1507553 | 1590600 | 1557681 | 1648956 | 147837 | 1556633 | 93.5 |
|  | 0 | 1622024 | 1659430 | 1732751 | 1740236 | 156591 | 1664070 | 100.0 |
| BT/Lap$^R$ | 10 | 1032464 | 1117009 | 1137209 | 1139456 | 110653 | 1106535 | 92.5 |
| 1.0 | 0 | 1137956 | 1191829 | 1230731 | 1194819 | 122773 | 1196615 | 100.0 |
| MDA-MB-361 | 10 | 420320 | 423604 | 472624 | 461509 | 459483 | 447508 | 104.1 |
|  | 0 | 402997 | 429160 | 446144 | 429977 | 441034 | 429862 | 100.0 |
| SK-BR3 | 10 | 1937000 | 2054461 | 2105337 | 2128527 | 211132 | 2067329 | 83.8 |
|  | 0 | 2275919 | 2477176 | 2507850 | 2556480 | 252281 | 2468047 | 100.0 |
| SK/Lap$^R$ | 10 | 934459 | 1005533 | 1044437 | 1098307 | 105641 | 1051172 | 94.2 |
| 1.0 | 0 | 858893 | 984583 | 1075111 | 1181353 | 122175 | 1115700 | 100.0 |
| MDA-MB-453 | 10 | 2644764 | 2710604 | 2763721 | 2789907 | 277195 | 2736190 | 82.8 |
|  | 0 | 2894653 | 3278459 | 3246290 | 3306141 | 338843 | 3304832 | 100.0 |
|  | Lapatinib |  |  |  | 0 |  |  |  |

| Cell | Example 30 (μM) | RLU | | | | | Average | Survival rate % | CDI |
|---|---|---|---|---|---|---|---|---|---|
| BT474 | 10 | 398377 | 392813 | 409887 | 415611 | 444171 | 412172 | 24.8 | 1.05 |
|  | 0 | 412434 | 392000 | 415243 | 442519 | 426263 | 417692 | 25.1 |  |
| BT/Lap$^R$ | 10 | 598830 | 589681 | 617719 | 609377 | 608990 | 604919 | 50.6 | 1.03 |
| 1.0 | 0 | 620030 | 626799 | 621089 | 658350 | 647589 | 634771 | 53.0 |  |
| MDA-MB-361 | 10 | 288984 | 301731 | 291331 | 297614 | 306466 | 297225 | 69.1 | 0.94 |
|  | 0 | 302584 | 295553 | 303233 | 301683 | 309791 | 302569 | 70.4 |  |
| SK-BR3 | 10 | 610944 | 595881 | 594551 | 631641 | 634386 | 613481 | 24.9 | 1.13 |
|  | 0 | 620929 | 634466 | 661000 | 652027 | 675276 | 648740 | 26.3 |  |
| SK/Lap$^R$ | 10 | 609037 | 638566 | 657327 | 858149 | 886574 | 634977 | 56.9 | 0.65 |
| 1.0 | 0 | 633107 | 910516 | 1026481 | 105341 | 1147684 | 103452 | 92.7 |  |
| MDA-MB-453 | 10 | 1215769 | 1250183 | 105341 | 130180 | 1233723 | 121098 | 36.6 | 1.26 |
|  | 0 | 1036211 | 1128233 | 113422 | 133323 | 1171624 | 116070 | 35.1 |  |
|  | Lapatinib |  |  |  | 1 |  |  |  |  |

Example 46: Measurement of Affinity Between Compounds of Examples and Hsp70

Materials and Method

1. Instrument: BIACORE T100 biomolecular interaction analyzer (GE, USA)
2. Reagents: PBS Buffer (×10), P20, CM5 chip (GE, USA), Hsp70 (human, ADI-ESP-550-D), manufactured by Enzo Life Sciences.

Formulation of Compound 30 mM mother liquor of compound was formulated with DMSO, which was diluted to 2 mM application solution with DMSO before use. 5 μl of the application solution was taken and diluted with 95 μl 1.05×PBS to 100 μM, and then diluted in turn with PBS containing 5% DMSO to 10, 3, 1, 0.3, 0.1, 0.03, 0.01, 0.003 μM, 0.3 μM. PBS containing 5% DMSO was used as solvent control.

Operating Procedures

1. Coupling of Hsp70 Protein and CM5 Chip

Hsp70 protein was diluted with 10 mmol/L sodium acetate buffer solution (pH 5.0) to 30 μg/ml, and coupled directly on a hydrophilic carboxylmethyl dextran matrix sensor chip M5 through normalized primary amine coupling reaction, RU=11209, and then the chip was balanced for 1-2 h with PBS Buffer at constant current.

2. Measurement of Affinity Between Compound and Hsp70 Protein

At a flow rate of 30 μl/ml, with PBS containing 5% DMSO as mobile phase, at 25° C., the compound was introduced in the sequence of 0.003, 0.01, 0.03, 0.1, 0.3, 1, 3 and 10 μM, with binding time 90 seconds, and dissociation time 120 seconds.

3. Result Analysis:

According to binding characteristics between the compounds and protein, the binding constant (equilibrium dissociation constant KD) between drugs and protein was calculated by selecting steady state model with the formula: Conc*Rmax/[conc+KD]+offset.

4. The results of preliminary screening showed that, among the compounds of Examples as screened, the compounds of Example 1, Example 2, Example 3, Example 5, Example 6, Example 13, Example 30 and Example 42, at 10 μm, produced an effect equivalent to that of positive compound VER-155008 (as reported in the literature, it was a compound having a definite binding to Hsp70, Cancer Chemother Pharmacol 2010, 66: 535-545). This indicated that the affinity for Hsp70 of the compounds of the above Examples was equivalent to that of the positive compound VER-155008 (literature value 0.3 μM).

5. Measurement of Affinity of Compounds for HSP70 Protein (KD Value)

At a flow rate of 30 μl/ml, PBS containing 5% DMSO as mobile phase, at 25° C., the compound was injected in the order of 0.003, 0.01, 0.03, 0.1, 0.3, 1, 3, and 10 μM, with the binding time of 90 sec, and the dissociation time of 120 sec. The affinities of 44 screened compounds for HSP70 protein were measured (the results were shown in Table 2).

TABLE 2

| Name of compound | KD (mol/L) |
|---|---|
| VER-155008 | $3.00 \times 10^{-7}$ |
| Example 1 | $2.191 \times 10^{-6}$ |
| Example 2 | $2.466 \times 10^{-7}$ |
| Example 3 | $5.248 \times 10^{-7}$ |
| Example 6 | $1.272 \times 10^{-5}$ |
| Example 13 | $5.199 \times 10^{-7}$ |
| Example 30 | $2.249 \times 10^{-7}$ |
| Example 42 | $4.339 \times 10^{-7}$ |

Although specific embodiments of the present invention have been described in detail, a person skilled in the art will appreciate that, according to all the teachings that have been disclosed, various modifications and substitutions can be conducted to the details, and all of these changes are within the protection scope of the present invention. The entire scope of the present invention is given by the appended claims and any equivalents thereof.

What is claimed is:

1. A method for resisting/reversing drug resistance of breast cancer cells in cells, which comprises administering to the cells an effective amount of the compound of formula (I),

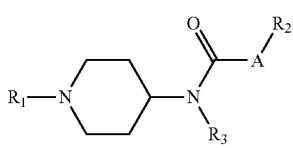

wherein:
A represents $CH_2$, S, O,

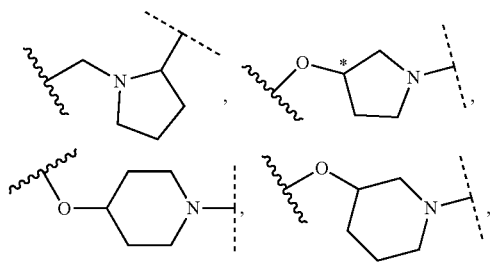

wherein "- - -" terminal is attached to $R_2$;

$R_1$ represents aryl, aromatic heterocyclyl, arylalkyl, or aromatic heterocyclylalkyl, wherein said aryl, aromatic heterocyclyl, arylalkyl, or aromatic heterocyclylalkyl is unsubstituted or substituted with one or two substituents independently selected from the group consisting of halogen, nitro, hydroxy, amino, cyano, alkyl, alkoxy, alkylthio, alkylamino, cycloalkoxy, cycloalkylthio, cycloalkylamino, alkenyl and alkynyl;

$R_2$ represents hydrogen, alkyl, cycloalkyl, substituted cycloalkyl, alkoxy, alkoxycarbonyl, alkanoyl, substituted alkanoyl, aliphatic heterocyclyl, substituted aliphatic heterocyclyl, aliphatic heterocyclylalkyl, aryl, substituted aryl, arylalkyl, substituted arylalkyl, arylsulfonyl, substituted arylsulfonyl, arolyl, substituted arolyl, aromatic heterocyclyl, substituted aromatic heterocyclyl, aromatic heterocyclylalkyl, aromatic heterocyclylsulfonyl, aromatic heterocyclylacyl; wherein the substituent includes alkyl, halogen, nitro, cyano, amino, hydroxy, alkoxy, mono($C_1$-$C_6$)alkylamino, di($C_1$-$C_6$)alkylamino, $C_2$-$C_6$alkenyl, $C_2$-$C_6$alkynyl, $C_1$-$C_6$haloalkyl, $C_1$-$C_6$haloalkoxy, aromatic heterocyclylalkyl;

$R_3$ represents hydrogen, $C_1$-$C_3$alkyl, or $C_3$-$C_6$cycloalkyl, or a pharmaceutically acceptable salt or a solvate thereof.

2. The method according to claim 1, wherein the cells are cell lines, or cells from a subject.

3. The method according to claim 1, wherein the method is carried out in vitro.

4. The method according to claim 1, wherein the method is carried out in vivo.

* * * * *